(12) United States Patent
Kataoka et al.

(10) Patent No.: US 11,096,991 B2
(45) Date of Patent: Aug. 24, 2021

(54) NANOREACTOR USING POLYION COMPLEX POLYMERSOMES, AND METHOD FOR PRODUCING SAME

(71) Applicant: THE UNIVERSITY OF TOKYO, Bunkyo-ku (JP)

(72) Inventors: Kazunori Kataoka, Tokyo (JP); Yasutaka Anraku, Tokyo (JP); Daiki Sueyoshi, Tokyo (JP)

(73) Assignee: THE UNIVERSITY OF TOKYO, Bunkyo-ku (JP)

( * ) Notice: Subject to any disclaimer, the term of this patent is extended or adjusted under 35 U.S.C. 154(b) by 478 days.

(21) Appl. No.: 15/571,217

(22) PCT Filed: May 6, 2016

(86) PCT No.: PCT/JP2016/063684
§ 371 (c)(1),
(2) Date: Jan. 5, 2018

(87) PCT Pub. No.: WO2016/178431
PCT Pub. Date: Nov. 10, 2016

(65) Prior Publication Data
US 2018/0140680 A1 May 24, 2018

(30) Foreign Application Priority Data
May 7, 2015 (JP) .............................. JP2015-095278

(51) Int. Cl.
*A61K 38/46* (2006.01)
*A61K 47/42* (2017.01)
*A61K 9/127* (2006.01)
*A61P 35/00* (2006.01)

(52) U.S. Cl.
CPC .............. *A61K 38/46* (2013.01); *A61K 9/127* (2013.01); *A61K 47/42* (2013.01); *A61P 35/00* (2018.01); *C12Y 302/0102* (2013.01)

(58) Field of Classification Search
CPC combination set(s) only.
See application file for complete search history.

(56) References Cited

U.S. PATENT DOCUMENTS

| 9,782,358 | B2 * | 10/2017 | Kataoka | .................. | C08L 77/04 |
|---|---|---|---|---|---|
| 2002/0110551 | A1 | 8/2002 | Chen | | |
| 2013/0122103 | A1 | 5/2013 | Kishimura et al. | | |
| 2013/0202711 | A1 | 8/2013 | Kataoka et al. | | |
| 2015/0190530 | A1 | 7/2015 | Ventosa Rull et al. | | |
| 2015/0258219 | A1 | 9/2015 | Kataoka et al. | | |
| 2016/0051484 | A1 | 2/2016 | Kataoka et al. | | |

FOREIGN PATENT DOCUMENTS

| JP | 1-246226 | 10/1989 |
|---|---|---|
| JP | 2004-503598 | 2/2004 |
| WO | WO 02/05841 A1 | 1/2002 |
| WO | WO 2011/145745 A1 | 11/2011 |
| WO | WO 2012/014942 A1 | 2/2012 |
| WO | WO 2013/006763 A1 | 1/2013 |
| WO | WO 2014/001509 A1 | 1/2014 |
| WO | WO 2014/058079 A1 | 4/2014 |
| WO | WO 2014/133172 A1 | 9/2014 |

OTHER PUBLICATIONS

Capizzi, R. Leukemia and Lymphoma 1993, vol. 10, Suppl. pp. 147-150.*
Extended European Search Report dated Nov. 27, 2018 in Patent Application No. 16789567.1, 14 pages.
Chuanoi, S. et al. "Fabrication of Polyion Complex Vesicles with Enhanced Salt and Temperature Resistance and Their Potential Applications as Enzymatic Nanoreactors" Biomacromolecules, vol. 15, No. 7, XP002786286, 2014, pp. 2389-2397.
Harada, A. et al. "Novel Polyion Complex Micelles Entrapping Enzyme Molecules in the Core: Preparation of Narrowly-Distributed Micelles from Lysozyme and Poly(ethylene glycol)-Poly(aspartic acid) Block Copolymer in Aqueous Medium" Macromolecules, American Chemical Society, vol. 31, No. 2, XP002935122, 1998, pp. 288-294.
Koide, A. et al. "Semipermeable Polymer Vesicle (PICsome) Self-Assembled in Aqueous Medium from a Pair of Oppositely Charged Block Copolymers: Physiologically Stable Micro-/Nanocontainers of Water-Soluble Macromolecules" Journal of the American Chemical Society, vol. 128, No. 18, XP002786287, 2006, pp. 5988-5989.
Harada, A. et al. "Functional control of enzyme-incorporated polyion complex micelles by applying electric field as external stimulus" Abstracts of Papers American Chemical Society, vol. 227, part 1, XP9509160, 2004, 1 page.
Anraku, Y. et al. "Systemically Injectable Enzyme-Loaded Polyion Complex Vesicles as In Vivo Nanoreactors Functioning in Tumors" Angew. Chem. Int. Ed., vol. 55, No. 2, XP002786288, 2016, pp. 560-565.
Anraku, Y. et al. "Spontaneous Formation of Nanosized Unilamellar Polyion Complex Vesicles with Tunable Size and Properties" Journal of the American Chemical Society, vol. 132, No. 5, XP055106735, 2010, pp. 1631-1636.
International Search Repot dated Jul. 19, 2016 in corresponding PCT/JP2016/063684 (with English translation).
Kimiyoshi Ichida, Febuxostat (TMX-67), Purcase (PeG-uricase). Japanese Journal of Clinical Medicine, 2008, vol. 66, No. 4, pp. 759-765 (with English abstract and partial English translation).

* cited by examiner

*Primary Examiner* — Heidi Reese
(74) *Attorney, Agent, or Firm* — Oblon, McClelland, Maier & Neustadt, L.L.P.

(57) ABSTRACT

The present invention provides a nanoreactor (nano size reaction field) using a polyion complex polymersome and a method for producing the nanoreactor. The present invention provides a polyion complex polymersome encapsulating e.g., an enzyme, in which the enzyme is an enzyme acting on a substance passing through a membrane of the polyion complex polymersome, as a substrate.

37 Claims, 17 Drawing Sheets

| Sample | Diffusion time (μS) | Fluorescence intensity per molecule (kHz) |
|---|---|---|
| (i) | 229.201 ± 1.422 | 49.223 |
| (ii) | 7965.647 ± 451.920 | 99.413 |

* Numeral indicated on the upper left side of each of the images represents EDC equivalent.

| Feeding Concentration (mg/mL) | FPEG6 Particle size (nm) | FPEG6 PdI | FPEG12 Particle size (nm) | FPEG12 PdI | FPEG20 Particle size (nm) | FPEG20 PdI | FPEG42 Particle size (nm) | FPEG42 PdI |
|---|---|---|---|---|---|---|---|---|
| 0.5 | 107 ± 3.2 | 0.073 ± 0.022 | 110 ± 2.3 | 0.108 ± 0.028 | 107 ± 4.5 | 0.049 ± 0.031 | 109 ± 3.1 | 0.093 ± 0.014 |
| 1 | 109 ± 2.9 | 0.072 ± 0.031 | 108 ± 4.2 | 0.085 ± 0.034 | 111 ± 3.2 | 0.067 ± 0.029 | 112 ± 2.2 | 0.102 ± 0.026 |
| 3 | 108 ± 4.3 | 0.087 ± 0.024 | 109 ± 4.3 | 0.106 ± 0.028 | 109 ± 3.9 | 0.074 ± 0.019 | 114 ± 3.6 | 0.05 ± 0.022 |
| 5 | 109 ± 2.4 | 0.101 ± 0.018 | 113 ± 3.6 | 0.076 ± 0.02 | 114 ± 2.8 | 0.096 ± 0.033 | 110 ± 5.2 | 0.04 ± 0.041 |
| 10 | 108 ± 6.2 | 0.112 ± 0.047 | 209 ± 23.2 | 0.228 ± 0.22 | 191 ± 11.2 | 0.253 ± 0.25 | 207 ± 9.2 | 0.243 ± 0.31 |

Fig. 10

Dynamic Light Scattering measurement (DLS)

Fluorescent Correlation Spectroscopy (FCS)

A α-Glucosidase

B Uricase

NANOREACTOR USING POLYION COMPLEX POLYMERSOMES, AND METHOD FOR PRODUCING SAME

TECHNICAL FIELD

The present invention relates to a nanoreactor using a polyion complex polymersome and a method for producing the nanoreactor.

BACKGROUND ART

For maintaining a stably of a protein of interest in the blood and inside the body and allowing its enzyme activity to exert in the blood, various needs are present in the medical and industrial fields and various techniques have been developed. For example, Patent Literature 1 provides nanocapsules encapsulating alcohol oxidase and catalase enzymes. The nanocapsule of Patent Literature 1 is proposed as a means for treating symptoms such as hangover and acute alcohol intoxication by decomposing an alcohol in the blood. Patent Literature 2 describes a technique for encapsulating a drug and a nucleic acid in a vesicle for use in drug delivery. Patent Literature 3 describes a vesicle formed of a water soluble and charged polymer, as a technique for reducing environmental load and the number of steps for forming the vesicle.

CITATION LIST

Patent Literature

Patent Literature 1: WO2013/6763
Patent Literature 2: WO2011/145745
Patent Literature 3: WO2012/14942

SUMMARY OF INVENTION

Technical Problem

The present invention provides a nanoreactor (nano-size reaction field) using a polyion complex polymersome, as a technique for allowing an enzyme to exhibit the activity stably for a long time in the blood while preventing outside leakage of a molecule encapsulated in a vesicle, and a method for producing the nanoreactor.

Solution to Problem

The present inventors found that, in the blood, a polyion complex polymersome encapsulating an enzyme can stabilize the enzyme encapsulated therein for a long time, and that the activity of the enzyme can be maintained for a long time. The present inventors also have found that permeability of a substance can be controlled depending upon the degree of crosslinking of a cationic polymer and an anionic polymer constituting a polyion complex polymersome. The present inventors have revealed that a polyion complex polymersome encapsulating L-asparaginase can extremely efficiently hydrolyze asparagine in the blood. The present inventors further have revealed that other enzymes can be encapsulated in the polyion complex polymersomes and the retention time of the enzymes in the blood increases by encapsulation and the enzyme activities thereof can be satisfactorily maintained. The present invention was achieved based on these findings.

More specifically, the present invention provides the following inventions.

(1) A polyion complex polymersome encapsulating an enzyme, in which the enzyme is an enzyme acting on a substance passing through membrane of the polyion complex polymersome, as a substrate.

(2) The polyion complex polymersome according to (1) above, in which the enzyme has a molecular weight of 5 kDa or more.

(3) The polyion complex polymersome according to (1) or (2) above, in which the substrate for the enzyme has a molecular weight of 1 kDa or less.

(4) The polyion complex polymersome according to any one of (1) to (3) above, in which the enzyme is a spherical protein.

(5) The polyion complex polymersome according to (1) above, in which the enzyme is selected from the group consisting of L-asparaginase, uricase, α-galactosidase and α-glucosidase.

(6) The polyion complex polymersome according to any one of (1) to (5) above, in which the polyion complex polymersome is a polyion complex polymersome of
a polymer (A) containing an amino acid having a COOH group at a side chain as a monomer unit, and
a polymer (B) containing an amino acid having a $NH_2$ group at a side chain as a monomer unit.

(7) The polyion complex polymersome according to (6) above, in which 50% or more of the COOH groups present in the polymer (A) are crosslinked with the $NH_2$ groups of the polymer (B).

(8) The polyion complex polymersome according to any one of (1) to (7) above, in which, in measurement in a 10 mM phosphate buffer solution (pH 7.4) at 37° C., a cumulative release rate (3) of the enzyme encapsulated 7 days after contact with the aqueous solution is 203 or less.

(9) The polyion complex polymersome according to (7) above, in which, in measurement in a 10 mM phosphate buffer solution (pH 7.4) at 37° C., a release rate constant k of a linear polyethylene glycol having a number average molecular weight of 2 kDa is $5 \times 10^{-3}$ or less.

(10) The polyion complex polymersome according to any one of (1) to (9) above, in which the enzyme encapsulated acts on a blood plasma component as a substrate.

(11) A pharmaceutical composition containing the polyion complex polymersome according to (10) above.

(12) The pharmaceutical composition according to (11) above, in which the pharmaceutical composition is a pharmaceutical composition to be administered to a patient with a disease caused by deficiency or abnormality of an enzyme, and the enzyme is an enzyme, which is deficient or has an abnormality in the patient.

(13) The pharmaceutical composition according to (11) above, in which the enzyme is an enzyme selected from the group consisting of L-asparaginase, uricase, α-galactosidase and α-glucosidase.

(14) The pharmaceutical composition according to (11) above, in which the enzyme is an enzyme decomposing a nutrient required for growth of a neoplasm or a microorganism.

(15) The pharmaceutical composition according to (13) above, in which the enzyme is L-asparaginase, for use in treating an asparagine-requiring tumor.

(16) The pharmaceutical composition according to (15) above, in which the asparagine-requiring tumor is a tumor in which the expression level of an asparagine-producing enzyme is 80% or less of the expression level of the enzyme in a normal cell.

(17) The pharmaceutical composition according to (15) or (16) above, in which the asparagine-requiring tumor is selected from the group consisting of acute lymphocytic leukemia, T cell malignant lymphoma, NK cellular leukemia and acute myelogenous leukemia.

(18) The pharmaceutical composition according to (11) or (12) above, in which the enzyme is α-galactosidase, for use in treating a disease caused by abnormality of α-galactosidase.

(19) The pharmaceutical composition according to (11) or (12) above, in which the enzyme is uricase, for use in treating hyperuricemia or a disease caused by hyperuricemia.

(20) The pharmaceutical composition according to (11) or (12), in which the enzyme is α-glucosidase, for use in treating a disease caused by abnormality of α-glucosidase.

According to the present invention, the enzyme supplemented by the pharmaceutical composition of the present invention is advantageous in that the enzyme has high stability in the blood, and immunogenicity of an enzyme even produced in a heterologous organism can be lowered.

BRIEF DESCRIPTION OF DRAWINGS

FIG. 10 shows the relationship between size of the molecule to be encapsulated, the concentration of use thereof, and the particle size of the polyion complex polymersome obtained.

FIG. 12 shows the cases of PEG6 (molecular weight: 6 k), PEG20 (molecular weight: 20 k) and PEG42 (molecular weight: 42 k). In the figure, "LC" represents the release rate from a polyion complex polymersome having a crosslinking degree of less than 40%; and "HC" represents the release rate from a polyion complex polymersome having a crosslinking degree of 80% or more. "FPEG" stands for fluorescein-labeled PEG.

In FIG. 15, a circle represents the release rate constant at 4° C., a triangle at 25° C., a square at 37° C. and a rhombus at 50° C. Open marks indicate the release rate constant in the cases of PICsomes having a low crosslinking degree; whereas solid marks indicate the cases of PICsomes having a high crosslinking degree.

DETAILED DESCRIPTION OF THE INVENTION

Figure 1A:
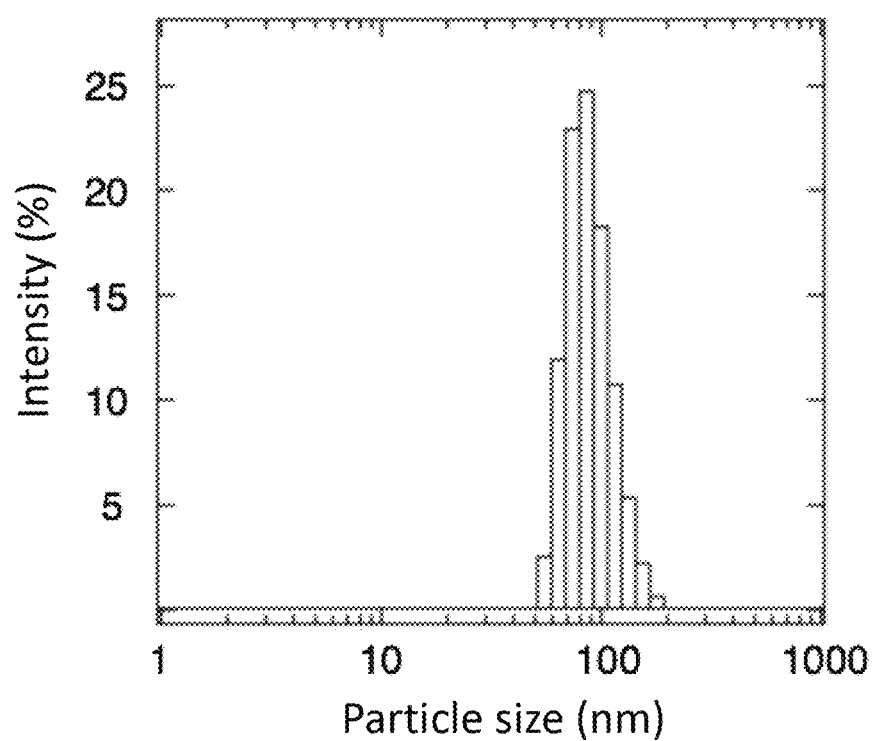
FIG. 1A shows the particle size distribution of a polyion complex polymersome encapsulating L-asparaginase.

In the specification, "polymer" refers to a molecule obtained by polymerization of a monomer unit and inclusively means a homo polymer, a copolymer and a block copolymer. In the specification, "homo polymer" refers to a polymer obtained by polymerizing a single type of monomer unit. In the specification, "copolymer" refers to a polymer obtained by polymerizing at least two types of monomer units and inclusively means a block copolymer. In the specification, "block copolymer" refers to a copolymer obtained by joining a block, which is formed by continuously connecting monomer units of the same type with another block, which is formed by continuously connecting monomer units of another type.

In the present invention, the "polyion complex polymersome", which is also called as PICsome, refers to a hollow fine particle formed of a polyion complex. It is known that the outer surface of a PICsome is preferably modified with polyethylene glycol in view of a retention time in blood.

In the specification, "polyion complex" (hereinafter also referred to as "PIC") is obtained by mixing a copolymer of PEG and an anionic block and a copolymer of PEG and a cationic block in an aqueous solution so as to neutralize the charge and has an ionic layer formed between a cationic block and an anionic block of both block copolymers. Binding PEG and the charged chain has a significance in suppressing aggregation and precipitation of a polyion complex and forming mono-dispersed nanoparticles having a particle size of several tens of nanometers and a core-shell structure. PEG herein, which covers the shell of a nanoparticle, is known to give the nanoparticle high biocompatibility and advantageously improve a retention time in blood of the nanoparticle. Also, it has been found that, in forming a polyion complex, one of the chargeable block copolymers does not require a PEG moiety, and a homo polymer, a surfactant, a nucleic acid and/or an enzyme may be used in place. In addition, in the polyion complex formation, at least one of the anionic polymer and the cationic polymer forms a copolymer with PEG. Both polymers may form a copolymer with PEG. PICsomes has a tendency to be formed under the conditions that the content of PEG is reduced. An enzyme can be encapsulated in a PICsome by mixing the PICsome and the enzyme and vigorously stirring the mixture. Stirring can be carried out by use of a stirrer such as a Vortex Mixer™. Alternatively, if a PICsome is formed in the presence of an enzyme, the enzyme can be encapsulated in the PICsome.

In the specification, "enzyme" refers to a protein having a catalytic activity. Generally, the molecular weight of the enzyme is known to have a wide distribution mainly around 10 kDa to 200 kDa.

In the specification, "subject" refers to a mammal including a human. The subject is a healthy subject or a subject having a disease.

The present inventors encapsulated an enzyme in a PICsome and brought a substrate for the enzyme into contact with the outer surface of the PICsome. As a result, they have found that the enzyme is maintained within the PICsome; however, the substrate, which is present outside the PICsome, passes through the membrane of the PICsome and successfully reacts with the enzyme within the PICsome; and the resultant reaction product can be released outside the PICsome. The present inventors have also found that the enzyme encapsulated in a PICsome is remarkably improved blood retention, compared to an unencapsulated enzyme.

Thus, according to the present invention, there is provided a polyion complex polymersome encapsulating an enzyme. According to the present invention, the enzyme can be an enzyme acting on a substance passing through the membrane of a polyion complex polymersome as a substrate.

According to the present invention, the permeability of PEG having a molecular weight of 6 kDa through the membrane of a PICsome was low. It is also predicted that the permeability of a non-fibrous protein through the membrane of a PICsome is further low. Thus, in an embodiment of the present invention, an enzyme having a molecular weight of 5 kDa or more, 10 kDa or more, 20 kDa or more, 30 kDa or more, 40 kDa or more, 50 kDa or more, 60 kDa or more, 70 kDa or more, 80 kDa or more, 90 kDa or more, 100 kDa or more, 110 kDa or more, 120 kDa or more, 130 kDa or more or 140 kDa or more can be used. If an enzyme has a molecular weight of 5 kDa or more, the enzyme can be maintained within a PICsome. The larger the molecular weight of an enzyme, the harder the enzyme to pass through the membrane of a PICsome and the easier the enzyme is maintained within the PICsome.

According to the present invention, the substrate for an enzyme is specified to have a molecular weight of less than 5 kDa, 4 kDa or less, 3 kDa or less, 2 kDa or less, 1 kDa or less, 750 Da or less, 500 Da or less, 400 Da or less, 300 Da or less or 200 Da or less. If a substrate has a molecular weight of less than 5 kDa, the substrate can pass though the membrane of a PICsome. The smaller the molecular weight of a substrate, the easier the substrate passes through the membrane of a PICsome, with the result that the substrate comes easily into contact with an enzyme, and a reaction efficiency increases.

According to the present invention, a fibrous polymer was advantageously maintained within a PICsome. A branched polymer can be more advantageously maintained within a PICsome since the permeability thereof through the membrane of PICsome is lower. Accordingly, in the present invention, a fibrous protein can be used as the enzyme; however, preferably a spherical protein can be used.

According to the present invention, the enzyme encapsulated in a PICsome is stable under physiological conditions and in the blood, compared to an unencapsulated enzyme. According to the present invention, the enzyme encapsulated in a PICsome is stable particularly in the blood, compared to an unencapsulated enzyme. Accordingly, in an embodiment of the present invention, the enzyme can be an enzyme acting on a plasma component as a substrate. By taking the constitution, an enzyme and activity thereof can be stably maintained in the blood and thus can effectively treat a substrate therefor in the blood.

In an embodiment of the present invention, L-asparaginase can be used as the enzyme. L-asparaginase (hereinafter sometimes referred to as "L-ASP") is a protein having a molecular weight of about 141 kDa, and hydrolyzes asparagine to produce aspartic acid and $NH_3$. L-ASP is commercially available as an agent for treating an acute lymphocytic leukemia, for example, under a trade name of Leunase™ from Kyowa Hakko Kirin Co., Ltd. L-ASP is also used in treating mastocytoma. L-ASP can be administered through intravenous injection.

It is considered that L-ASP is considered to produce an antitumor effect by hydrolyzing L-asparagine in the blood to induce nutritional deficiency in asparagine-requiring tumor cells. As the asparaginase, asparaginase derived from *E. coli* (*Escherichia coli*) and asparaginase derived from *Erwinia chrysanthemi*, can be used. However, these asparaginases derived from bacteria may possibly cause an allergic reaction in humans. According to the present invention, asparaginase is encapsulated in a PICsome, and thus, the problem of an allergic reaction becomes less important. As L-ASP, asparaginase modified with PEG may be used.

According to the present invention, L-ASP encapsulated in a PICsome (hereinafter sometimes referred to as "encapsulated L-ASP") exhibited high retentivity in the blood and high production ability of $NH_3$ (more specifically, asparagine hydrolytic ability), compared to unencapsulated L-ASP (hereinafter sometimes referred to as "free L-ASP"). Thus, according to the present invention, the encapsulated L-ASP can be more effectively used than the conventional L-ASP in treating asparagine-requiring or asparagine-sensitive tumor cells. Thus, according to the present invention, a pharmaceutical composition containing a PICsome encapsulating L-ASP as an enzyme is provided.

The pharmaceutical composition according to the present invention containing a PICsome encapsulating L-ASP as an enzyme can be used for treating an asparagine-requiring tumor. Examples of the asparagine-requiring tumor include acute leukemia such as acute lymphocytic leukemia, acute lymphoblastic leukemia, in particular pediatric acute lymphocytic leukemia, acute myelogenous leukemia, and other acute leukemias; and malignant lymphoma such as T cell malignant lymphoma, Hodgkin's disease, reticulosarcoma and lymphosarcoma.

Recently, it has been found that, in NK cellular leukemia and acute myelogenous leukemia in which an asparagine-producing enzyme is deficient or the expression thereof is low, it is easy to induce asparagine deficiency and cell death can be induced by administration of asparaginase in the tumor cells. Accordingly, in an embodiment of the present invention, an asparagine-requiring tumor can be identified by examining expression of an asparagine-producing enzyme. For example, in an embodiment of the present invention, an asparagine-requiring tumor can be a tumor exhibiting an expression level of an asparagine-producing enzyme of 80% or less, 70% or less, 60% or less, 50% or less, 40% or less, 30% or less, 20% or less, 10% or less, 5% or less, 3% or less or 1% or less of the expression thereof in normal cells. In an embodiment of the present invention, the asparagine-requiring tumor can be any one of NK cellular leukemia and acute myelogenous leukemia.

The pharmaceutical composition of the present invention containing a PICsome encapsulating L-ASP as an enzyme can be administered to a tumor patient as a subject, who exhibits an allergic symptom (for example, anaphylaxis symptom) by a chemical treatment using L-ASP.

Neoplasms and microorganisms, besides the neoplasm such as a tumor, can be killed or reduced by administering PICsome, which encapsulates an enzyme decomposing a nutrition source required by a microorganism such as a bacterium and a virus, into a living body.

In an embodiment of the present invention, uricase can be used as the enzyme to be encapsulated. Uricase (EC1.7.33), which is also called as urate oxidase, can decompose uric acid involved in metabolism of purine and caffeine. Because of this, uricase can be used for treating hyperuricemia showing a high uric acid level in the blood and a disease caused by hyperuricemia (for example, complication). Examples of the disease caused by hyperuricemia include gout (for example, gouty nodule and gouty arthritis) and urate deposition disease and uric acid stone, interstitial nephritis, kidney failure, and arteriosclerosis. According to the present invention, there is provided a pharmaceutical composition containing a PICsome encapsulating uricase as an enzyme, for use in treating hyperuricemia or a disease caused by hyperuricemia.

Since the enzyme encapsulated in a PICsome is stable in the blood, the PICsome can be effectively used for transporting the enzyme encapsulated therein from the blood to the interior of a cell. There are many enzymes within a cell, in particular, within a lysosome. If deficiency or abnormality of any one of the enzymes occurs, a lysosomal disease occurs. Accordingly, in an embodiment of the present invention, the enzyme whose deficiency or abnormality (for example, low enzyme activity) causes a lysosomal disease, is encapsulated in a PICsome and can be administered to a subject with the lysosomal disease caused by deficiency or abnormality of the enzyme.

In an embodiment of the present invention, as the enzyme to be encapsulated, an enzyme present within a lysosome, for example, α-galactosidase (hereinafter also referred to as "α-GAL") can be used. α-Galactosidase (EC3.2.1.22) has an activity to hydrolyze α-D-galactoside and an activity to accelerate transfer via O of α-D-galactoside to various alcohol derivatives. α-Galactosidase causes a lysosomal disease, i.e., Fabry's disease, if the activity is absent. α-Galactosidase can improve the symptom of Fabry's disease or suppress progression of the symptom by a replacement therapy by drip infusion.

According to the present invention, a pharmaceutical composition containing a PICsome encapsulating α-galactosidase as an enzyme can be used for treating a disease such as a lysosomal disease (for example, Fabry's disease) caused by decrease or deficiency of α-galactosidase activity. According to the present invention, there is provided a pharmaceutical composition containing a PICsome encapsulating α-galactosidase as an enzyme, for use in treating a disease (for example, a lysosomal disease) caused by abnormality of α-galactosidase.

In an embodiment of the present invention, α-glucosidase can be used as the enzyme to be encapsulated. α-Glucosidase (EC3.2.1.20) has an activity to hydrolyze an α-1,4-glucoside bond of sugars. α-Glucosidase causes a lysosomal disease (for example, Pompe disease (OMIM No.: 232300)) if the activity is absent. Accordingly, α-glucosidase can be used for treating a disease caused by abnormality of α-glucosidase (for example, activity is low or absent). Examples of the disease caused by low or deficient activity of α-glucosidase include a lysosomal disease (for example, Pompe disease). Thus, according to the present invention, there is provided a pharmaceutical composition containing a PICsome in which α-glucosidase is used as an enzyme, for use in treating a disease caused by low or deficient activity of α-glucosidase.

The enzymes of the present invention are not limited to those described herein, and a wide variety of enzymes can be used in enzyme replacement therapies for making up for an enzyme not sufficiently present due to deficiency or abnormality thereof, in vivo.

As a block copolymer forming a PICsome, a block copolymer of a PEG block and a polycation block, and a homopolyanion; or a block copolymer of a PEG block and a polyanion block, and a homopolycation, can be exemplified. As the block copolymer, a biodegradable block copolymer is preferably used. Various copolymers are known as the biodegradable block copolymer and any one of them can be used in principal.

In the present invention, examples of the polycation block include a polymer block having a cationic natural amino acid and a cationic non-natural amino acid such as histidine, tryptophan, ornithine, arginine, lysine, and/or a group represented by —(NH—(CH$_2$)$_2$)$_p$—NH$_2$ {where p represents an integer of 1 to 5} as a cationic side chain; more specifically, a cationic non-natural amino acid polymer block having the aforementioned cationic side chain; more specifically, a cationic non-natural amino acid polymer block such as aspartic acid or glutamic acid having the cationic side chain. In an embodiment of the present invention, a polycation block is a polymer block having a group represented by —(NH—(CH$_2$)$_2$)$_p$—NH$_2$ {where p represents an integer of 1 to 5} as a side chain. As the cationic natural amino acid herein, preferably histidine, tryptophan, ornithine, arginine and lysine; more preferably, arginine, ornithine and lysine; further preferably, ornithine and lysine; and still further preferably lysine can be used. As the biodegradable block copolymer having high biocompatibility, for example, a poly(aspartic acid-tetraethylene pentamine) block copolymer, and a polyethylene glycol-poly((5-aminopentyl)-aspartic acid) block copolymer, can be used.

The polycation block may contain a cationic amino acid and an amino acid having a cationic side chain in combination. More specifically, in an embodiment of the present invention, the polycation block is a polymer of a monomer unit containing a cationic natural amino acid, a cationic non-natural amino acid, or a cationic natural amino acid and a cationic non-natural amino acid. In an embodiment of the present invention, the bond between monomer units in a polycation block is a peptide bond. In a preferable embodiment of the present invention, the cationic non-natural amino acid is an amino acid having a group represented by —(NH—(CH$_2$)$_2$)$_p$—NH$_2$ {where n represents an integer of 1 to 5} as a side chain. In an embodiment of the present invention, the polycation block can be a polycation block obtained by polymerizing a cationic natural amino acid, aspartic acid and glutamic acid modified with a group represented by —(NH—(CH$_2$)$_2$)$_p$—NH$_2$ {where p represents an integer of 1 to 5}, in any order. In an embodiment of the present invention, 40%, 50%, 60%, 70%, 80%, 90%, 95%, 98 or 100% of the monomer unit of a polymer has a group represented by —(NH—(CH$_2$)$_2$)$_p$—NH$_2$ {where p represents an integer of 1 to 5}, as a side chain.

In an embodiment of the present invention, a polyion complex, which consists of a block copolymer of a PEG block and a polycation block and a homopolyanion, can form a PICsome. In a specific embodiment of the present invention, the block copolymer of a PEG block and a polycation block can be a copolymer of a PEG block and a poly(aminopentyl-aspartic acid). In a specific embodiment of the present invention, the homopolyanion can be poly (aspartic acid). In a further specific embodiment of the present invention, a block copolymer of a PEG block and a polycation block, and the homopolyanion can be a copolymer of a PEG block and a poly(aminopentyl-aspartic acid) and poly(aspartic acid), respectively, in a PICsome. In the further specific embodiment of the present invention, the polymerization degrees of the PEG block, poly(aspartic acid) block and poly(aminopentyl-aspartic acid) block can be each independently an integer of 5 to 20,000, preferably an integer of 10 to 5,000, more preferably an integer of 40 to 500, further preferably an integer of 5 to 1,000 and still further preferably an integer of 10 to 200.

In the present invention, as the polycation block, for example, a PEG-poly(N'—[N-(2-aminoethyl)-2-aminoethyl]-aspartic acid) block copolymer (PEG-P(Asp-DET)) can be used. PEG-P(Asp-DET) can be prepared in accordance with a usual way (see, Chem. Med. Chem. 1 (2006) 439-444).

In P(Asp-DET), Asp-DET is aspartic acid wherein a carboxyl group at the side chain is substituted by a diethyl triamine (DET) group (—NH—CH$_2$—CH$_2$—NH—CH$_2$—CH$_2$—NH$_2$). The structure of P(Asp-DET) is represented by the following chemical formula.

P(Asp-DET)

[Formula 1]

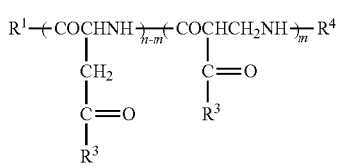

(I)

where

R$^1$ is a hydroxyl group, a protecting group, a hydrophobic group or a polymerizable group, R$^4$ is H, a protecting group, a hydrophobic group or a polymerizable group, R$^3$ is a group represented by —(NH—(CH$_2$)$_2$)$_2$—NH$_2$, n is an integer of 0 to 5000, for example, an integer of 0 to 500, m is an integer of 0 to 5000, for example, an integer of 0 to 500, m+n is an integer of 2 to 5000, for example, an integer of 2 to 500, and n−m is an integer of 0 or more.

In the formula, individual repeating units are described in a specific order for the sake of convenience; however, individual repeating units may be present in random order, and may be the same or different.

In the case where a polycation block and polyethylene glycol form a copolymer, R$^1$ or R$^4$ represents a bond, and polyethylene glycol and a polycation block can form a copolymer via the bond. Note that, in the polymer represented by the above general Formula (I), individual repeating units are connected via a peptide bond.

In an embodiment of the present invention, after a PICsome is formed, the cationic polymer and the anionic polymer in the PICsome may be crosslinked. The crosslinking can be appropriately carried out by a method known to those skilled in the art. For example, the PICsome of the present invention can be formed by using a cationic polymer that may be modified with PEG and an anionic polymer that may be modified with PEG, followed by crosslinking the cationic polymer and the anionic polymer. In an embodiment of the present invention, the PICsome may be formed by mixing a polymer (cationic polymer), which contains a cationic amino acid having a NH$_2$ group at the side chain as a monomer unit and which may be modified with PEG, and a polymer, which contains an anionic amino acid having a COOH group at a side chain as a monomer unit and which may be modified with PEG, in an aqueous solution, followed by crosslinking the cationic polymer and the anionic polymer by using 1-ethyl-3-(3-dimethylaminopropyl) carbodiimide hydrochloride as a crosslinking agent. Crosslinking can be carried out after an enzyme is encapsulated in a PICsome.

Accordingly, in an embodiment of the present invention, the PICsome may be a PICsome formed of a polymer (A) containing an amino acid having a COOH group at a side chain as a monomer unit, and a polymer (B) containing an amino acid having a NH$_2$ group at a side chain as a monomer unit.

In the embodiment, in order to crosslink the polymer (A) and the polymer (B), 1-ethyl-3-(3-dimethylaminopropyl) carbodiimide hydrochloride (EDC) can be used.

The crosslinking degree (%) between a cationic polymer and an anionic polymer in a PICsome can be calculated, for example, with reference to a spectrum of a PEG-PAsp polymer (not crosslinked) obtained by Fourier transform infrared spectroscopy (FT-IR), by obtaining the ratio of the peak derived from a carboxyl group (1600 cm$^{-1}$; derived from stretching vibration of a COO$^-$ group) relative to the peak derived from PEG (1460 cm$^{-1}$; derived from deformation vibration of a C—H group). The crosslinking degree can be enhanced by increasing the amount of crosslinking agent to be used.

According to the present invention, there is provided a method of decreasing permeability of a molecule through the membrane of a PICsome, or a method of decreasing a release rate of a molecule from a PICsome, each including crosslinking a cationic polymer and an anionic polymer constituting the PICsome. In an embodiment of the present invention, the permeability of a molecule of less than 5 kDa, 4 kDa or less, 3 kDa or less, 2 kDa or less, 1 kDa or less, 750

Da or less, 500 Da or less, 400 Da or less, 300 Da or less or 200 Da or less can be maintained at 50% or more, 60% or more, 70% or more, 80% or more, or 90% or more, or substantially. In an embodiment of the present invention, as a molecule whose permeability is to be decreased or whose release rate is to be decreased, a molecule of 5 kDa or more, 10 kDa or more, 20 kDa or more, 30 kDa or more, 40 kDa or more, 50 kDa or more, 60 kDa or more, 70 kDa or more, 80 kDa or more, 90 kDa or more, 100 kDa or more, 110 kDa or more, 120 kDa or more, 130 kDa or more or 140 kDa or more can be used.

According to the present invention, as the crosslinking degree (%) between a cationic polymer and an anionic polymer constituting a PICsome increases, the release rate of a molecule from the PICsome decreases, as well as the release rate constant decreases. For example, the crosslinking degree (%) can be 25% or more, 30% or more, 40% or more, 50% or more, 60% or more, 70% or more or 80% or more. The crosslinking proportion may be 90% or more. If the crosslinking degree exceeds 40%, the release rate constant significantly decreases. Therefore, the crosslinking degree (%) is preferably large and can be preferably, 50% or more, 60% or more, 70% or more or 80% or more.

According to the present invention, the release amount of enzyme encapsulated in a PICsome, from the PIC some, can be reduced by increasing the crosslinking degree between the cationic polymer and the anionic polymer constituting a PICsome. A PICsome having a cumulative release rate (%) of 60% or less, 50% or less, 40% or less, 30% or less, 20% or less, 10% or less or 5% or less, which is a value obtained in the measurement in a 10 mM phosphate buffer solution (pH 7.4) at 37° C. on the 7th day after contact with the aqueous solution, can be provided. According to the present invention, there is provided a PICsome having a release rate constant k of a linear polyethylene glycol having a number average molecular weight of 2 kDa, wherein the release rate constant k is $5 \times 10^{-3}$ or less, $4 \times 10^{-3}$ or less, $3 \times 10^{-4}$ or less, $2 \times 10^{-1}$ or less or $1 \times 10^{-1}$ or less, in case where the release rate constant k is measured in a 10 mM phosphate buffer solution (pH 7.4) at 37° C. In an embodiment, an enzyme having 5 kDa or more, 10 kDa or more, 20 kDa or more, 30 kDa or more, 40 kDa or more, 50 kDa or more, 60 kDa or more, 70 kDa or more, 80 kDa or more, 90 kDa or more, 100 kDa or more, 110 kDa or more, 120 kDa or more, 130 kDa or more or 140 kDa or more can be used as the enzyme.

According to another aspect of the present invention, there is provided a composition containing a PICsome for use in encapsulating L-ASP. In this aspect, in an embodiment, the PICsome can be the PICsome of the present invention. In this aspect, the composition can be used for encapsulating L-ASP in a PICsome by mixing the PICsome with L-ASP. Asparagine, even if it is present outside a PICsome, can pass through the membrane of the PICsome and reach the interior thereof, and thus, the composition of the present invention can be used in hydrolyzation of asparagine by allowing it into contact with asparagine.

According to another aspect of the present invention, there is provided a composition containing a PICsome, for use in encapsulating α-galactosidase. In this aspect, in an embodiment, the PICsome can be the PICsome of the present invention. In this aspect, the composition can be used for encapsulating α-galactosidase in a PICsome by mixing the PICsome with α-galactosidase. A substrate (for example, globotriaosylceramide), even if it is present outside a PICsome, can pass through the membrane of the PICsome and reach the interior thereof, and thus, the composition of the present invention can be used for hydrolysis of asparagine by allowing it in contact with α-galactosidase.

In an embodiment of the present invention, there is provided a composition containing a PICsome, for use in encapsulating uricase. In this aspect, in an embodiment, the PICsome can be the PICsome of the present invention. In this aspect, the composition of the present invention can be used for encapsulating uricase in a PICsome by mixing the PICsome with uricase. A substrate (for example, uric acid), even if it is present outside a PICsome, can pass through the membrane of the PICsome and reach the interior thereof, and thus, the composition of the present invention can be used for hydrolysis of urea by allowing it in contact with uricase.

In an embodiment of the present invention, there is provided a composition containing a PICsome, for use in encapsulating α-glucosidase. In this aspect, in an embodiment, the PICsome can be the PICsome of the present invention. In this aspect, the composition of the present invention can be used for encapsulating α-glucosidase in a PICsome by mixing the PICsome with α-glucosidase. A substrate (for example, glycogen), even if it is present outside a PICsome, can pass through the membrane of the PICsome and reach the interior thereof, and thus, the composition of the present invention can be used for hydrolysis of α-1,4-glucoside bond by allowing it in contact with α-galactosidase.

According to another aspect of the present invention, there is provided a composition containing L-ASP for use in encapsulating it in a PICsome. In this aspect, in an embodiment, the PICsome can be the PICsome of the present invention. In this aspect, the composition can be used for encapsulating L-ASP in a PICsome by mixing the PICsome with L-ASP. Asparagine, even if it is present outside a PICsome, can pass through the membrane of the PICsome and reach the interior thereof, and thus, the composition of the present invention can be used for hydrolysis of asparagine by allowing it in contact with asparagine.

In an embodiment of the present invention, there is provided a composition containing α-galactosidase, for use in encapsulating it in a PICsome. In this aspect, in an embodiment, the PICsome can be the PICsome of the present invention. In this aspect, the composition can be used for encapsulating α-galactosidase in a PICsome by mixing the PICsome with α-galactosidase. A substrate even if it is present outside a PICsome, can pass through the membrane of the PICsome and reach the interior thereof, and thus, the composition of the present invention can be used for hydrolysis of the substrate by allowing it in contact with α-galactosidase.

In an embodiment of the present invention, there is provided a composition containing uricase for use in encapsulating it in PICsome. In this aspect, in an embodiment, the PICsome can be the PICsome of the present invention. In this aspect, the composition can be used for encapsulating uricase in a PICsome by mixing the PICsome with uricase. Urea, even if it is present outside a PICsome, can pass through the membrane of the PICsome and reach the interior thereof, and thus, the composition of the present invention can be used for hydrolysis of urea by allowing it in contact with uricase.

In an embodiment of the present invention, there is provided a composition containing α-glucosidase, for use in encapsulating it in a PICsome. In this aspect, in an embodiment, the PICsome can be the PICsome of the present invention. In this aspect, the composition can be used for encapsulating α-glucosidase in a PICsome by mixing the PICsome with uricase. A substrate, even if it is present outside a PICsome, can pass through the membrane of the PICsome and reach the interior thereof, and thus, the composition of the present invention can be used for hydrolysis of the substrate by allowing it in contact with α-glucosidase.

According to another aspect of the present invention, there is provided a combination of a polycation that may be modified with PEG, a polyanion and L-ASP. According to another aspect of the present invention, there is provided a combination of a polycation, a polyanion that may be modified with PEG and L-ASP. The combination of the present invention can be used for preparing a PICsome encapsulating L-ASP.

In an embodiment of the present invention, there is provided a combination of a polycation that may be modified with PEG, a polyanion and α-galactosidase. In an embodiment of the present invention, there is provided a combination of a polycation that may be modified with PEG, a polyanion and uricase. There is provided a combination of a polycation that may be modified with PEG, a polyanion and α-glucosidase.

In an embodiment of the present invention, there is provided a combination of a polycation, a polyanion that may be modified with PEG and α-galactosidase. In an embodiment of the present invention, there is provided a combination of a polycation, a polyanion that may be modified with PEG and uricase. In an embodiment of the present invention, there is provided a combination of a polycation, a polyanion that may be modified with PEG and α-glucosidase. These combinations can be used for preparing PICsomes encapsulating the enzyme as described above.

According to a still another aspect of the present invention, there is provided a method for treating a subject including administering the PICsome of the present invention encapsulating an enzyme to a subject requiring administration of the enzyme. The subject can be a subject suffering from a disease caused by absence of a specific enzyme or a lowered expression level of the enzyme.

The enzymes may include L-ASP. The diseases may include an asparagine-requiring tumor. Thus, according to the present invention, there is provided a method for treating an asparagine-requiring tumor, including administering an effective amount of PICsome containing L-ASP to a subject requiring L-ASP. Examples of the asparagine-requiring tumor include acute leukemia such as acute lymphocytic leukemia, acute lymphoblastic leukemia, in particular, pediatric acute lymphocytic leukemia, acute myelogenous leukemia, other acute leukemias; and malignant lymphoma such as T cell malignant lymphoma, Hodgkin's disease, reticulosarcoma and lymphosarcoma. The asparagine-requiring tumor may be a tumor in which the expression of an asparagine-producing enzyme is 80% or less, 70% or less, 60% or less, 50% or less, 40% or less, 30% or less, 20% or less, 10% or less, 5% or less, 3% or less or 1% or less of that in a normal cell. In an embodiment of the present invention, the subject may be a tumor patient presenting an allergic symptom (for example, anaphylaxis symptom) by a chemical treatment using L-APS.

Alternatively, The enzymes may include α-galactosidase. The diseases may include a disease (for example, Fabry's disease) caused by abnormality of α-galactosidase. Thus, according to the present invention, there is provided a method for treating a disease (e.g., a disease caused by low or deficient activity of α-galactosidase, such as a lysosomal disease (for example, Fabry's disease)) caused by abnormality of α-galactosidase, including administering an effective amount of PICsome containing α-galactosidase to a subject in need thereof. In an embodiment of the present invention, the subject may be a tumor patient presenting an allergic symptom (for example, anaphylaxis symptom) by a chemical treatment using α-galactosidase.

Alternatively, The enzymes may include uricase, which can be used for treating hyperuricemia and a disease caused by hyperuricemia. As the disease caused by hyperuricemia, diseases caused by hyperuricemia such as gout (for example, gouty nodule and gouty arthritis) and urate deposition disease and uric acid stone, interstitial nephritis, kidney failure, and arteriosclerosis. Thus, according to the present invention, there is provided a method for treating hyperuricemia and a disease caused by hyperuricemia, including administering an effective amount of PICsome containing uricase to a subject in need thereof. In an embodiment of the present invention, the subject may be a tumor patient presenting an allergic symptom (for example, anaphylaxis symptom) by a chemical treatment using uricase Alternatively, the enzymes may include α-glucosidase. The disease may include a disease (for example, Pompe disease) caused by abnormality of α-glucosidase. Thus, according to the present invention, there is provided a method for treating a disease (e.g., a disease caused by low or deficient activity of α-glucosidase such as a lysosomal disease (for example, Pompe disease)) caused by abnormality of α-glucosidase, including administering an effective amount of PICsome containing α-glucosidase to a subject in need thereof. In an embodiment of the present invention, the subject may be a tumor patient presenting an allergic symptom (for example, anaphylaxis symptom) by a chemical treatment using α-glucosidase.

In the specification, "treatment" refers to curing, preventing or inducing remission of a disease or a disorder or decreasing a progressing speed of a disease or a disorder. The treatment can be attained by administering a therapeutically effective amount of a pharmaceutical composition.

EXAMPLES

Example 1: Preparation of PICsome Encapsulating Enzyme

In this example, a PICsome encapsulating an enzyme, L-asparaginase (hereinafter also referred to as "L-ASP"), was prepared.

1. Synthesis of PEG-P (Asp)

First, a polyethylene glycol-poly(β-benzyl-L-aspartate) block copolymer (PEG-PBLA) was obtained by polymerization of β-benzyl-L-aspartate-N-carboxylic anhydride (BLA-NCA)(obtained by outsourcing to Chuo Kaseihin Co., Ltd.). More specifically, BLA-NCA (18.9 g) was dissolved in 20 mL of N,N'-dimethylformamide (DMF). Polyethylene glycol (Me-O-PEG-$NH_2$) (molecular weight 2,000) (2.0 g) having a methoxy group at an end and an aminoethyl group at the other end, was dissolved in DMF (20 mL). The resultant solution was added to the BLA-NCA solution. The solution mixture was kept at 35° C. to carry out the polymerization for 40 hours. After completion of the polymerization reaction was confirmed by infrared spectroscopy (IR) analysis, the reaction mixture was added dropwise to diethyl ether (2 L). The precipitated polymer was recovered by suction filtration, washed with diethyl ether and subjected to vacuum drying to obtain PEG-PBLA (15.51 g (yield 79%)).

Subsequently, from PEG-PBLA, a polyethylene glycol-poly(aspartic acid) block copolymer (PEG-P(Asp.)) was synthesized. More specifically, PEG-PBLA (1.0 g) was suspended in a 0.5 N sodium hydroxide to hydrolyze the benzyl ester at room temperature. After the copolymer was dissolved, dialysis was performed by using a dialysis membrane (fractionation molecular weight 6,000-8,000) against water. The solution within the membrane was subjected to lyophilization to obtain 654 mg (yield 78%) of PEG-P(Asp).

2. Synthesis of Homo P(Asp-AP)

First, a poly(β-benzyl-L-aspartate) (homo PBLA polymer) was obtained by polymerization of BLA-NCA. More specifically, 20 g of β-benzyl-L-aspartate-N-carboxylic anhydride (BLA-NCA) was dissolved in 33.3 mL of N,N'-dimethylformamide (DMF) and 300 mL of dichloromethane. N-butylamine (89.0 µL) was added to the BLA-NCA solution obtained above. The solution mixture was kept at 35° C. to carry out the polymerization for 40 hours. After completion of the polymerization reaction was confirmed by infrared spectroscopy (IR) analysis, the reaction mixture was added dropwise to 1 L of a hexane/ethyl acetate solution (hexane:ethyl acetate=6:4). The precipitated polymer was recovered by suction filtration, washed with diethyl ether and subjected to vacuum drying to obtain a homo PBLA polymer (14.82 g (79%)).

Subsequently, from the homo PBLA polymer obtained, a poly((5-aminopentyl)-aspartic acid)(homo P(Asp.-AP)) was synthesized. More specifically, homo PBLA (1 g) lyophilized with benzene was dissolved in 10 mL of N-methyl-2-pyrrolidone (NMP). DAP (17.2 mL) was dissolved in NMP (17.2 mL). The resultant solution was added to the homo PBLA solution. The solution mixture was kept at 5° C. to carry out the reaction for 40 minutes. Thereafter, to the reaction solution, a 20 wt % acetic acid aqueous solution (10 mL) was added and dialysis was performed by using a dialysis membrane (fractionation molecular weight 6,000-8,000) against water. The solution within the membrane was subjected to lyophilization to obtain 0.76 g (82%) of P(Asp.-AP).

3. Preparation of DyLight 488 Labeled L-ASP

L-asparaginase (L-ASP; manufactured by Sigma-Aldrich, Product No: A3809)(15 mg) was dissolved in 10 mL of a 10 mM phosphate buffer (PB, pH 7.4, 0 mM NaCl). DyLight 488-N-hydroxysuccinimide ester (manufactured by Thermo Scientific Product No: 46402) (2 mg) was dissolved in 1 mL of DMSO. The resultant solution was added to the L-ASP solution to perform a reaction at 25° C. for 4 hours. Thereafter, unreacted DyLight 488-N-hydroxysuccinimide ester molecules were removed by use of an ultrafiltration tube with a membrane of a fractionation molecular weight of 10,000.

4. Preparation of Cy5 Labeled L-ASP

L-ASP (75 mg) was dissolved in 50 mL of a 10 mM phosphate buffer (PB, pH 7.4, 0 mM NaCl). 20 Vial of Cy5-N-hydroxysuccinimide ester dye pack (manufactured by GE Healthcare, Product No: PA25001) was dissolved in 5 mL of DMSO. The resultant solution was added to the L-ASP solution to perform a reaction at 25° C. for 4 hours. Thereafter, unreacted Cy5-N-hydroxysuccinimide ester molecules were removed by use of an ultrafiltration tube with a membrane of a fractionation molecular weight of 10,000.

5. Preparation of L-ASP Encapsulated PICsome

PEG-P(Asp.) (20 mg) was dissolved in 20 mL of a 10 mM phosphate buffer (PB, pH 7.4, 0 mM NaCl) to prepare a 1 mg/mL PEG-P(Asp.) solution. Also, 30 mg of homo P(Asp.-AP) was dissolved in PB (50 mL) to prepare a 1 mg/mL homo P(Asp.-AP) solution. Subsequently, aliquots of 4.0 mL and 5.0 mL were taken from the PEG-P(Asp.) solution and the homo P(Asp.-AP) solution, respectively, added to a 50 mL conical tube, mixed and stirred by a Vortex mixer for 2 minutes (2000 rpm). This solution will be hereinafter referred to as an empty-PICsome solution.

Thereafter, L-ASP (32 mg) was dissolved in 5.7 mL of a 10 mM phosphate buffer (PB, pH 7.4, 0 mM NaCl) to prepare a 5.6 mg/mL L-ASP solution. Alternatively, a 10 mM phosphate buffer (PB, pH 7.4, 0 mM NaCl) solution of DyLight 488 labeled L-ASP or Cy5 labeled L-ASP was concentrated by ultrafiltration to prepare a 5.6 mg/mL fluorescent labeled L-ASP solution.

The 5.6 mg/mL L-ASP solution or the fluorescent labeled L-ASP solution (5.0 mL) was added to the empty-PICsome solution (9.0 mL), mixed and stirred by a Vortex mixer for 2 minutes (2000 rpm). Thereafter, a PB solution (5.6 mL) containing a water soluble condensing agent, EDC (10 mg/mL), was added and the mixture was allowed to stand still overnight to crosslink a polyion complex. Thereafter, a polymer not involved in formation of PICsomes, L-ASP not encapsulated in the PICsomes, EDC and others were removed by use of an ultrafiltration tube with a membrane of a fractionation molecular weight of 300,000.

Example 2: Characterization of PICsomes

In this Example, the size (Z average particle diameter) and polydispersity index (PDI) of the PICsomes obtained were determined by a Zetasizer (Malvern). The shape of the PICsomes was observed by a transmission electron microscope (TEM, JEM-1400) after stained with uranyl acetate.

1. Evaluation of L-ASP Encapsulated PICsome Obtained by Zetasizer

The size (Z average particle diameter) and polydispersity index (PDI) of the L-ASP enclosed PICsomes obtained were determined by a Zetasizer (Malvern). The size was obtained by measuring diffusion of particles moving in accordance with Brownian motion and converting the measurement results into a particle size and a particle size distribution by use of the Stokes-Einstein equation. The shape of a micelle was evaluated by using a transmission electron microscope (TEM, JEM-1400). The Z average particle diameter herein is the data obtained by analyzing the measurement data of a particle dispersion in accordance with a dynamic light scattering method by a cumulant analysis. In the cumulant analysis, an average value of particle sizes and polydispersity index (PDI) are obtained. In the present invention, the average particle diameter is defined as the Z average particle diameter. To be more specific, operation of fitting a polynomial to the logarithm of the G1 correlation function obtained by measurement is referred to as cumulant analysis.

In the following expression:

$$LN(G1)=a+bt+ct^2+dt^3+et^4+ \ldots$$

constant b is a secondary cumulant or a Z average diffusion coefficient. The value of the Z average diffusion coefficient is converted into a particle size by use of the viscosity of a dispersion medium and several equipment constants. The particle size is the Z average particle diameter and suitably used as a dispersion stability index for quality control.

Figure 1B:
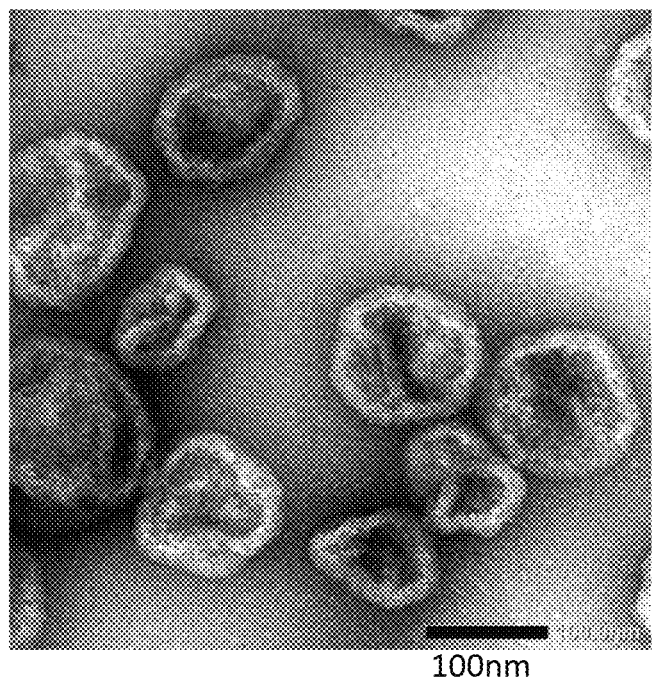
FIG. 1B shows a transmission electron microscope (TEM) image thereof.

The particle size distribution of the L-ASP encapsulated PICsomes obtained and transmission electron microscope (TEM) image thereof were as shown in FIG. 1A and FIG. 1B, respectively. As shown in FIG. 1A, the L-ASP encapsulated PICsomes obtained had a monodispersed particle size distribution having a mode value at a diameter of about 100 nm. In the TEM image shown in FIG. 1B, PICsomes having a diameter (particle size) of about 100 nm were frequently observed.

2. Confirmation of Encapsulation of L-ASP in PICsome

To confirm encapsulation of L-ASP in a PICsome, the diffusion rates of free L-ASP (L-ASP not encapsulated in a PICsome, also referred to as "free L-ASP") and L-ASP encapsulated in a PICsome (also referred to as "encapsulate L-ASP") in a solution, were evaluated by fluorescence correlation spectroscopy (FCS).

The fluorescence correlation spectroscopy was performed by use of a confocal laser scanning microscope (LSM 510 META/Confocal3, Carl Zeiss) having an Ar laser line (488 nm) installed therein, as follows. A sample solution was added dropwise to a 8-well chamber and irradiated with excitation light, and the fluorescence was detected by an objective lens immersed in water. Fluctuation of fluorescence intensity was analyzed by use of an autocorrelation function to calculate the diffusion time and fluorescence intensity per particle.

Figure 2:
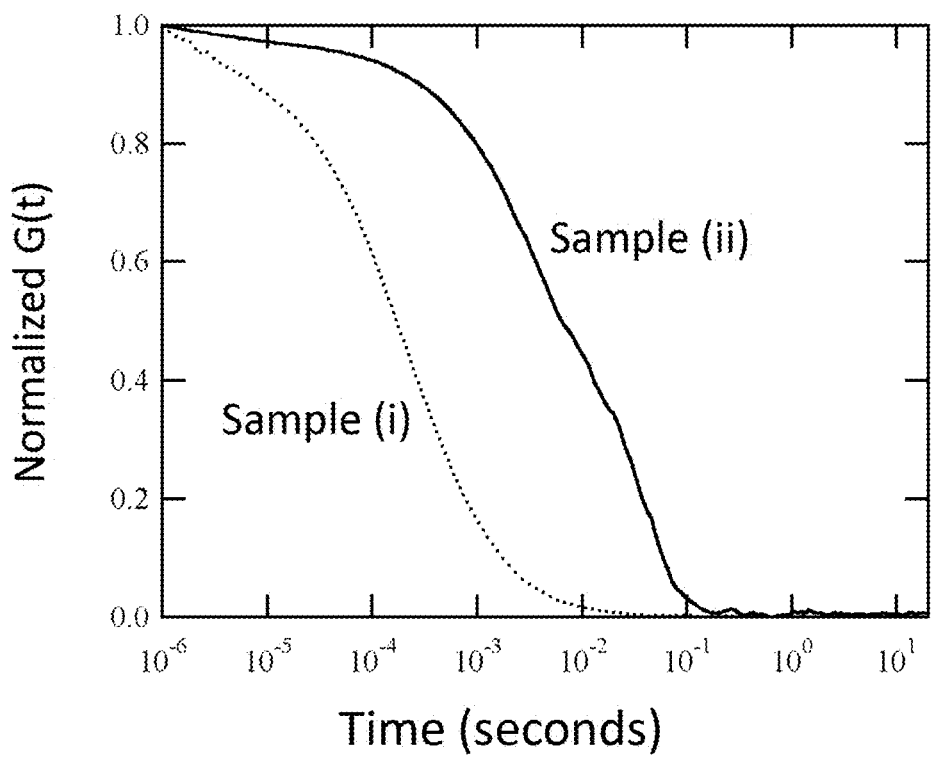
FIG. 2 shows the analytical results of L-asparaginase encapsulated in a polyion complex polymersome and L-asparaginase unencapsulated by fluorescence correlation spectroscopy.

The results were as shown in FIG. 2. In FIG. 2, sample (i) represents free L-ASP labeled with DyLight488; whereas, sample (ii) represents encapsulated L-ASP labeled with DyLight488. As shown in FIG. 2, encapsulated L-ASP showed a longer diffusion time and a stronger fluorescence intensity per particle (count per molecule) than free L-ASP. From this, it was confirmed that L-ASP is encapsulated in a PICsomes without fail From comparison of fluorescence intensity per particle, it was estimated that two L-ASP molecules are encapsulated in a single PICsome.

Next, the enzyme activity of each of free L-ASP and encapsulated L-ASP was evaluated. L-aspartic acid β-(7-amide-4-methyl coumarin) (also referred to as "Asp-AMC") is a substrate, which is decomposed by the enzyme activity of L-ASP to produce 7-amino-4-methyl coumarin (also referred to as "AMC") emitting fluorescence (Ex/Em=350 nm/450 nm). The Michaelis-Menten plot and Lineweaver-Burk plot with respect to the reaction with the substrate were prepared. More specifically, first, PBS solutions of Asp-AMC, free L-ASP, and encapsulated L-ASP were placed in a thermostatic chamber so that the temperature was 37° C. Thereafter, the Asp-AMC solution was mixed with the free L-ASP solution or the encapsulated L-ASP solution. From the solution mixture, an aliquot (predetermined amount) was taken and immediately poured to a 96 well plate (TECAN). The plate was placed in a multiplate reader, which had been kept at 37° C. in advance, and fluorescence intensity was measured periodically for a predetermined time. Using a calibration curve, which was previously prepared by using an AMC standard solution, a change of fluorescence intensity was converted into the production rate of a product. In this manner, the reaction rate V was obtained. Measurement was performed by changing the substrate concentration [S] variously. [S] was plotted on the horizontal axis and V was plotted on the vertical axis. The plot results were applied to the following expression to computationally obtain the Michaelis-Menten coefficient ($K_m$).

$$1/V=(K_m/V_{max})(1/[S])+1/V_{max} \qquad \text{[Expression 1]}$$

where $V_{max}$ is a maximum reaction rate to [S].

Figure 3A:
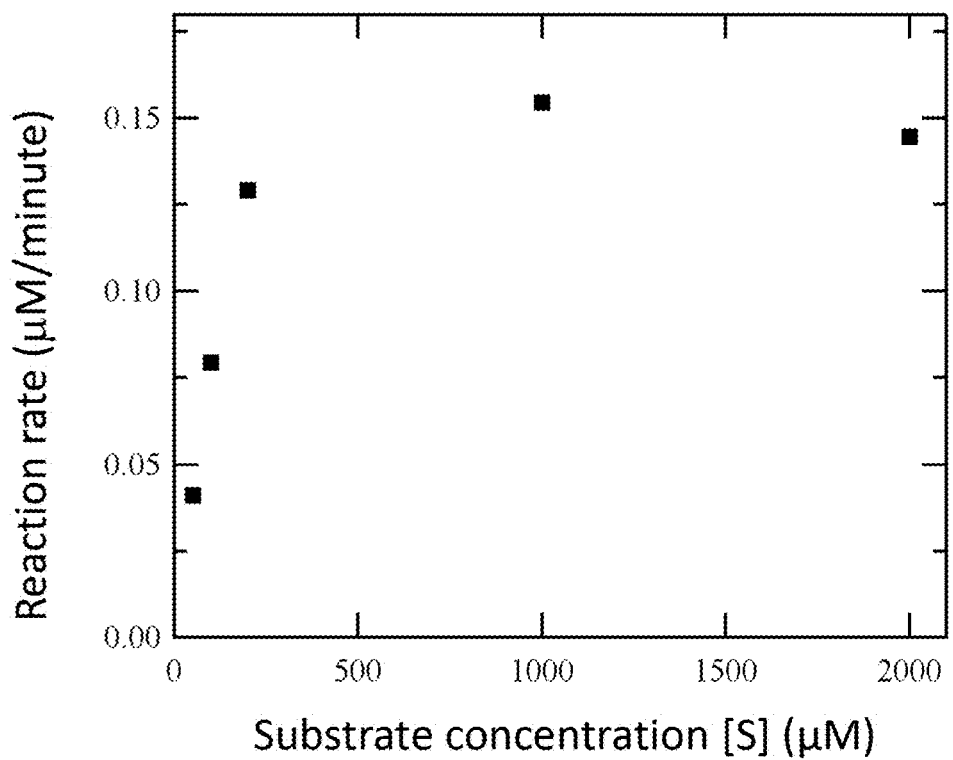
FIG. 3A shows the Michaelis-Menten plot of L-asparaginase unencapsulated.
Figure 3B:
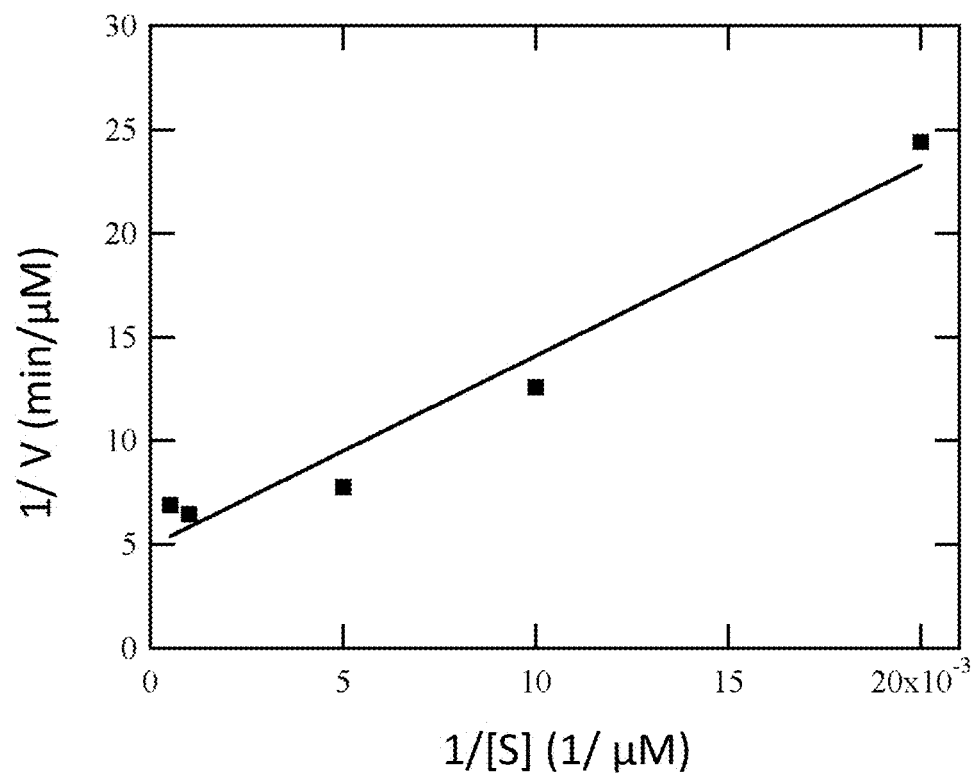
FIG. 3B shows Lineweaver-Burk plot thereof.
Figure 4A:
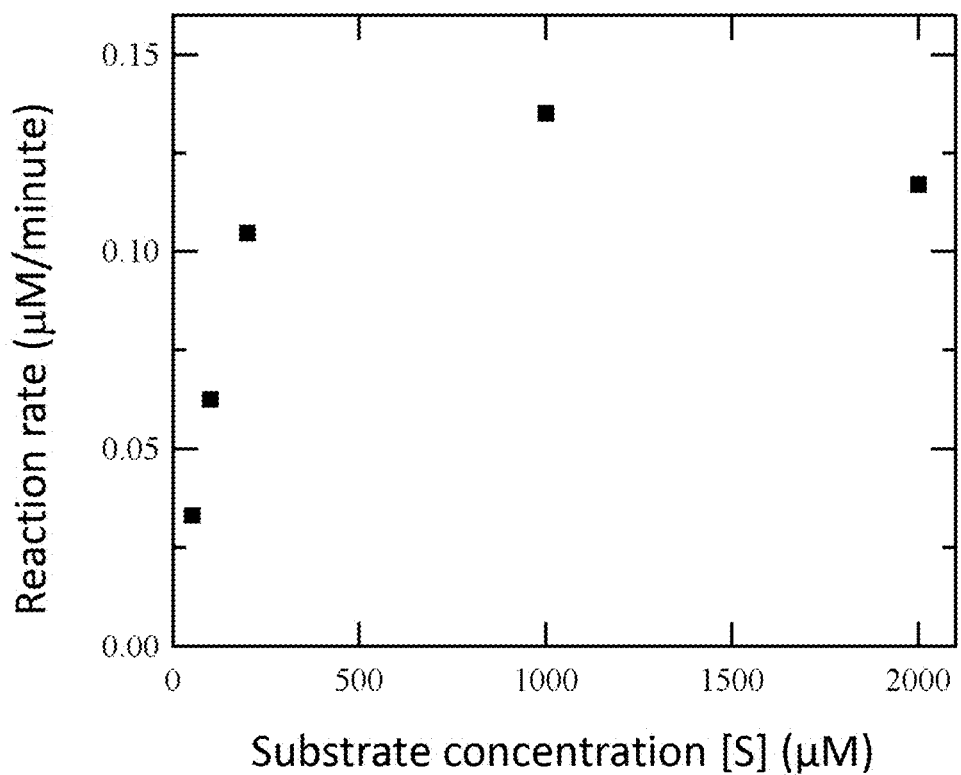
FIG. 4A shows Michaelis-Menten plot of L-asparaginase encapsulated in a polyion complex polymersome.
Figure 4B:
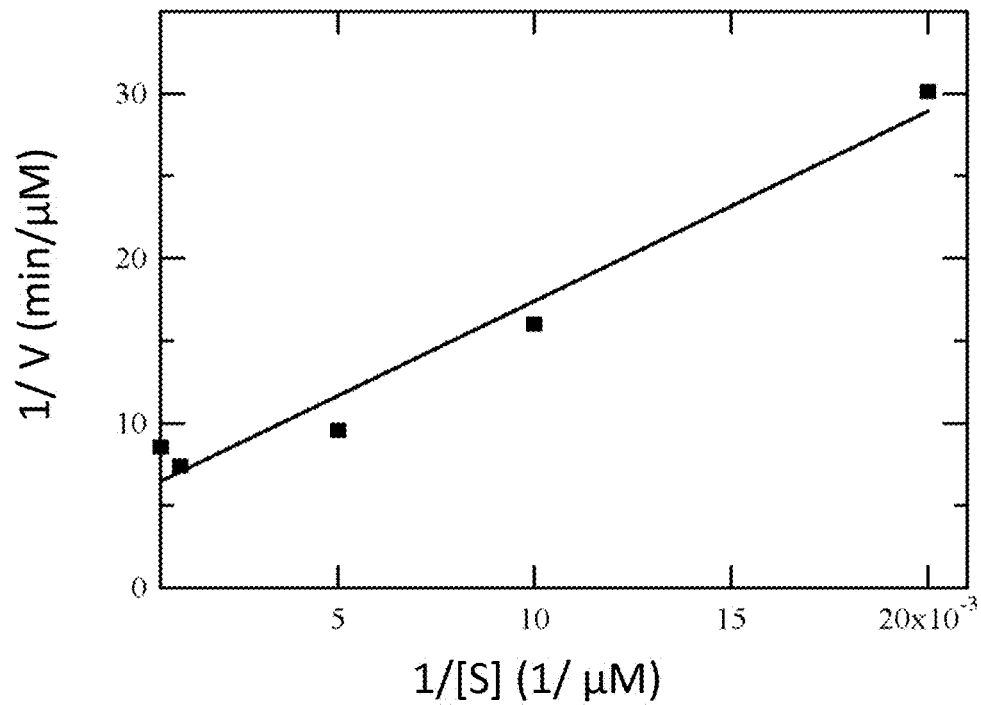
FIG. 4B shows Lineweaver-Burk plot thereof.

When the Michaelis-Menten plot (FIG. 3A) and the Lineweaver-Burk plot (FIG. 3B) of free L-ASP were compared to the Michaelis-Menten plot (FIG. 4A) and the Lineweaver-Burk plot (FIG. 4B) of encapsulated L-ASP, no significant difference in enzyme activity was observed. When Michaelis-Menten coefficients (Km) were individually calculated, the Km value of the free L-ASP was 186 μM; whereas the Km value of the encapsulated L-ASP was 194 μM. From this, it was found that encapsulated L-ASP has almost the same enzyme activity as free L-ASP.

3. Blood Retention of L-ASP Encapsulated in PICsome

Using mice, blood retention of free L-ASP and encapsulated L-ASP was evaluated. Cy5-labeled free L-ASP (8 U) and Cy5-labeled encapsulated L-ASP (250 μg) (estimated weight of a polymer constituting a PiCsome) were administered to mice (Balb/c, 5 weeks old, n=5) through the tail vein. At the time of administration (time: 0), 3 hours and 24 hours after the administration, mice were sacrificed, and the blood was taken. The blood was centrifuged, and the supernatant was recovered and then the fluorescence intensity of the supernatant (Ex/Em=650 nm/670 nm) was measured by a multiplate reader (TECAN, M1000PRO). The results were as shown in FIG. 5.

Figure 5:
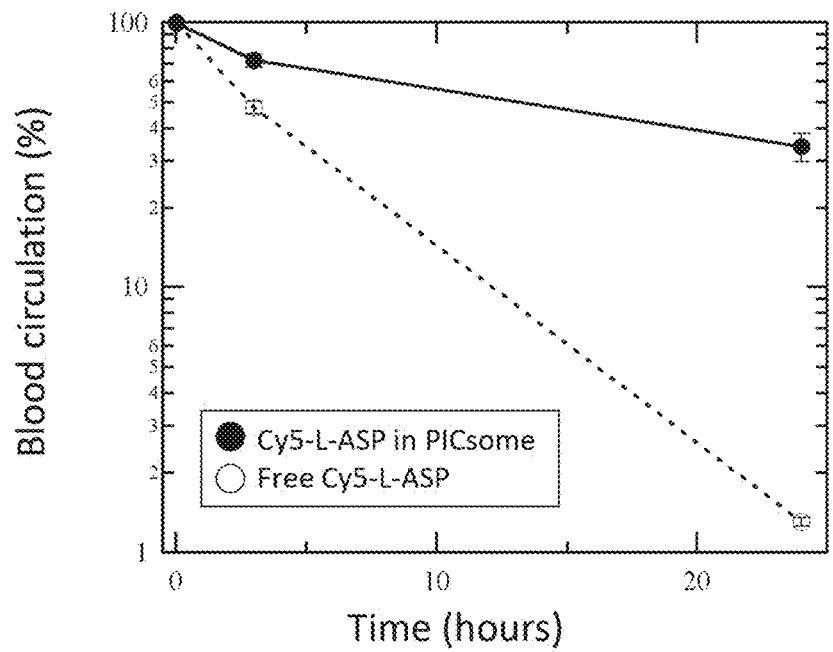
FIG. 5 shows blood retention of L-asparaginase encapsulated in a polyion complex polymersome.

FIG. 5 shows relative fluorescence intensity at individual time points based on the fluorescence intensity immediately after administration as 100%. As shown in FIG. 5, blood retention of encapsulated L-ASP was remarkably high compared to the blood retention of the free L-ASP.

4. Time-Dependent Change of Enzyme Activity Under Physiological Conditions

Free L-ASP and encapsulated L-ASP were dissolved in aqueous solutions containing 10% FBS at a concentration of 4.8 μg/mL and 2 mg/mL (estimated concentration of a polymer constituting a PICsome), respectively. The solutions were allowed to stand still at 37° C. for 0, 3 hours, 6 hours, 12 hours or 24 hours. Thereafter, using 1000 μM L-aspartic acid β-7-amide-4-methyl coumarin (Asp-AMC) (Sigma-Aldrich, A1057) as a substrate, the reaction rates of the enzyme at individual time points were obtained. The reaction rates at individual time points were standardized such that the reaction rate of the sample at the time point of 0 is 1, and relative reaction rates were obtained. The results were as shown in FIG. 6.

Figure 6:
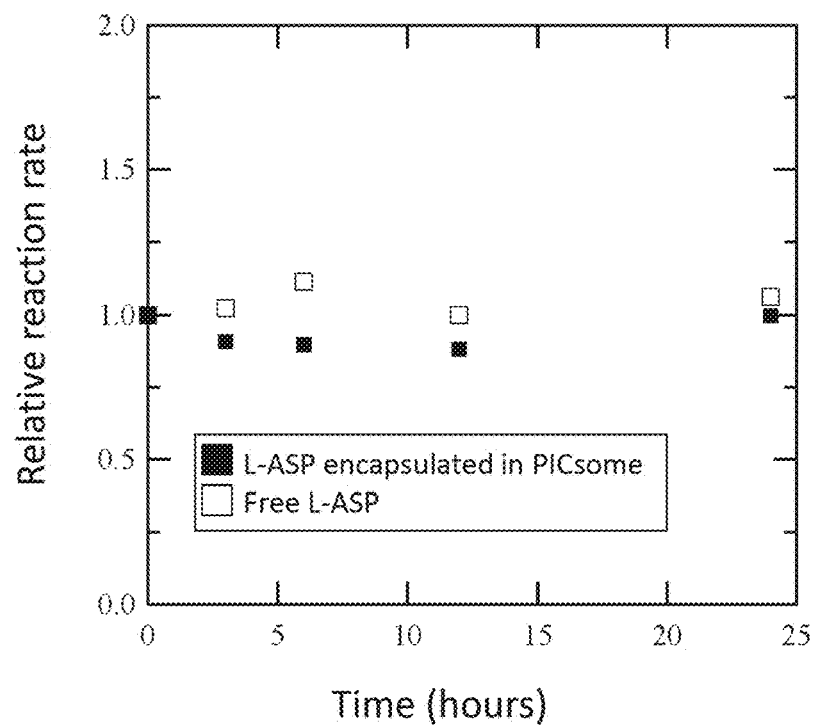
FIG. 6 shows a change of enzyme kinetics of L-asparaginase with time.

As shown in FIG. 6, free L-ASP and encapsulated L-ASP both successfully maintained enzyme activity in vitro for a long time under physiological conditions.

5. Enzyme Activity of L-ASP Encapsulated in PICsome in the Blood

Figure 7A:
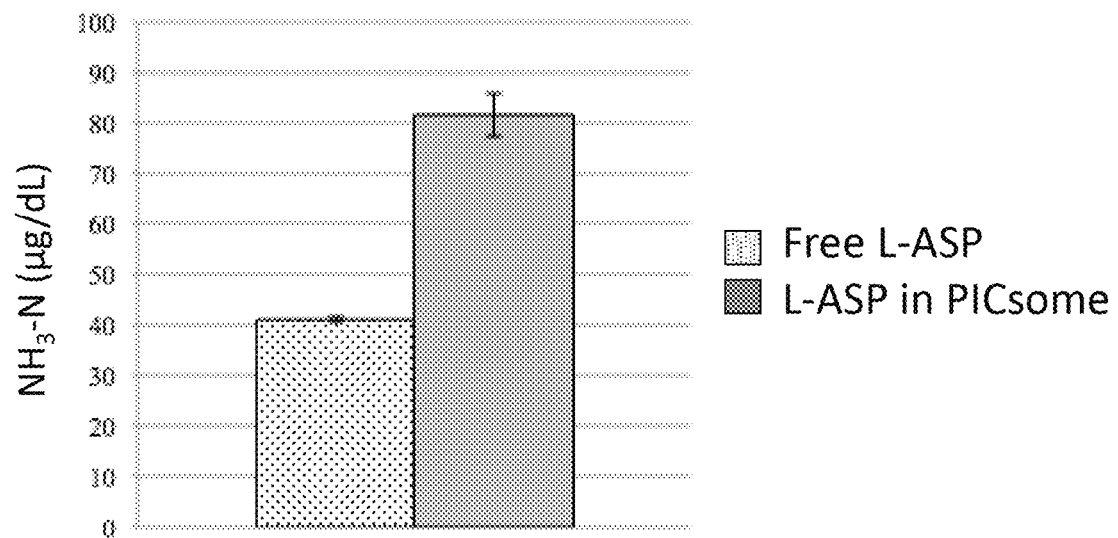
FIG. 7A shows blood ammonia nitrogen concentration in a mouse to which L-asparaginase is administered through the tail vein.
Figure 7B:
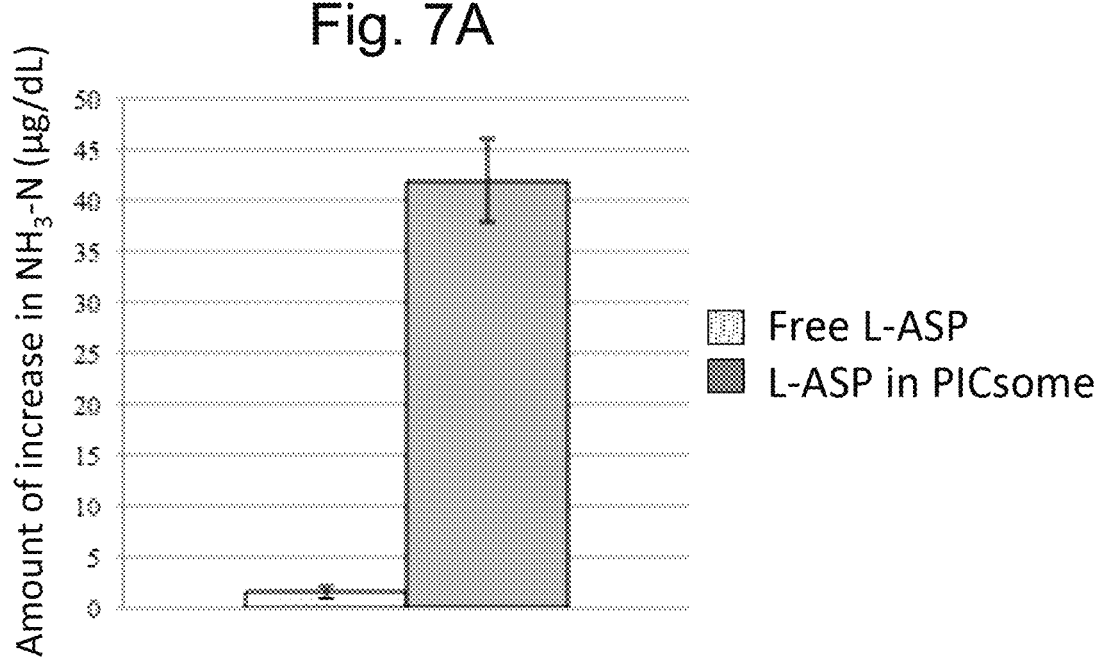
FIG. 7B shows an amount of increase in blood ammonia nitrogen concentration.

To mice (Balb/c, 5 weeks old, n=3), free L-ASP or encapsulated L-ASP was separately administered at a concentration of (100 U/kg) through the tail vein. Twenty four hours later, the blood ammonia nitrogen concentration ($NH_3$—N) was measured. More specifically, 24 hours after administration, mice were sacrificed, and blood was taken and centrifuged. The resultant supernatant (blood plasma) was recovered and the ammonia nitrogen concentration in the supernatant was measured with an automatic biochemical analyzer (Drichem) and calibrated with reference to the calibration curve previously prepared. The results were as shown in FIGS. 7A and 7B. Note that, it is known that L-ASP decomposes L-asparagine to produce L-aspartic acid and ammonia.

As shown in FIGS. 7A and 7B, the concentration of ammonia nitrogen in the blood plasma in a (mouse) group, to which encapsulated L-ASP was administered, was overwhelmingly higher than that of a free L-ASP administration group (FIG. 7A). The increased amount of ammonia nitrogen in the blood plasma was calculated based on the ammonia nitrogen concentrations before and after administration. As a result, as shown in FIG. 7B the plasma ammonia nitrogen concentration rarely increased in the free L-ASP administration group; whereas the plasma ammonia nitrogen concentration in the encapsulated L-ASP administration group dramatically increased. As described above, encapsulated L-ASP administered reacted with a plasma component and enzymatically converts the plasma component to successfully and efficiently generate ammonia nitrogen.

Example 3: Effect of Chemical Modification of PICsome on Enzymatic Reaction

L-ASP encapsulated PICsomes were prepared in the same manner as in Example 1 except that the concentration of a crosslinking agent, EDC, was changed. The relationship between a crosslinking degree and the properties of the PICsomes was examined.

Figure 8A:
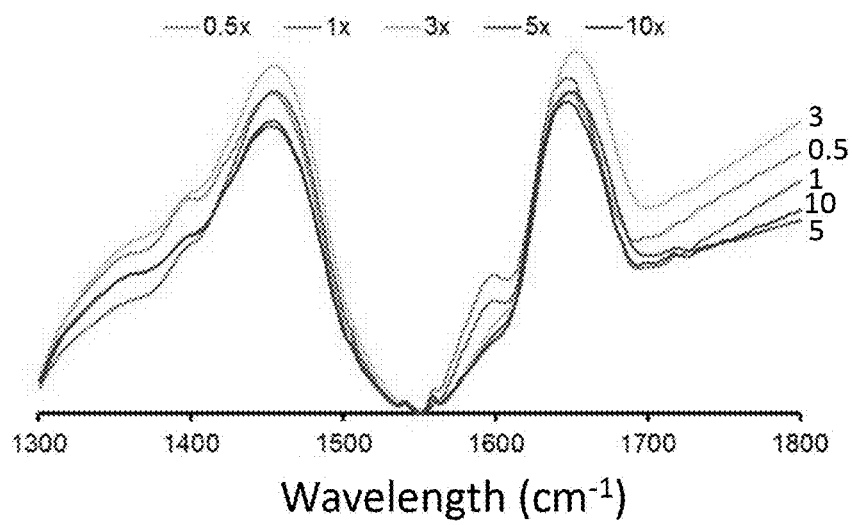
FIG. 8A shows the equivalents of a crosslinking agent, EDC, and the FT-IR spectrum of a polyion complex polymersome obtained.
Figure 8B:
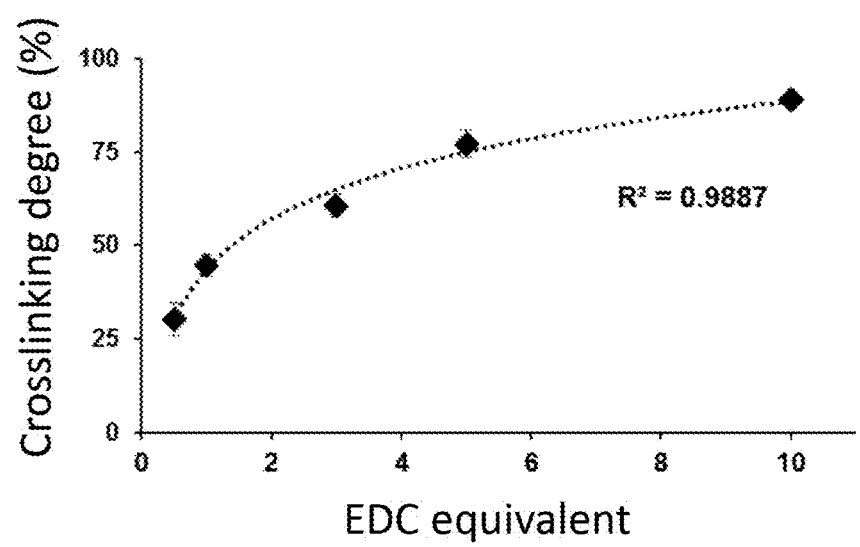
FIG. 8B shows the relationship between the crosslinking proportion (%) and the EDC equivalents.

The concentration of EDC in Example 1 was normalized as one (equivalent). PICsomes were obtained through treatments with EDC, which were 0.5 times, 3 times, 5 times and 10 times as large as the concentration of Example 1. The FT-IR spectra of them are shown in FIG. 8A. The relationship between EDC equivalent and the crosslinking degree is shown in FIG. 8B. The crosslinking proportion was calculated based on FT-IR. In FIG. 8B, the percentage (%) of crosslinked $COO^-$ groups to those present in the PEG-poly Asp copolymers is indicated as the crosslinking proportion.

As shown in FIGS. 8A and 8B, it was found that the crosslinking degree between molecules constituting a PICsome can be controlled by changing the amount of EDC to be used for crosslinking. At 0.5 equivalents, 30.2% of the $COO^-$ groups was crosslinked. At 1 equivalent, 44.5% of the $COO^-$ groups was crosslinked. At 3 equivalents, 60.5% of the $COO^-$ groups was crosslinked. At 5 equivalents, 77.1% of the $COO^-$ groups was crosslinked. At 10 equivalents, 89.1% of the $COO^-$ groups was crosslinked.

Figure 9A:
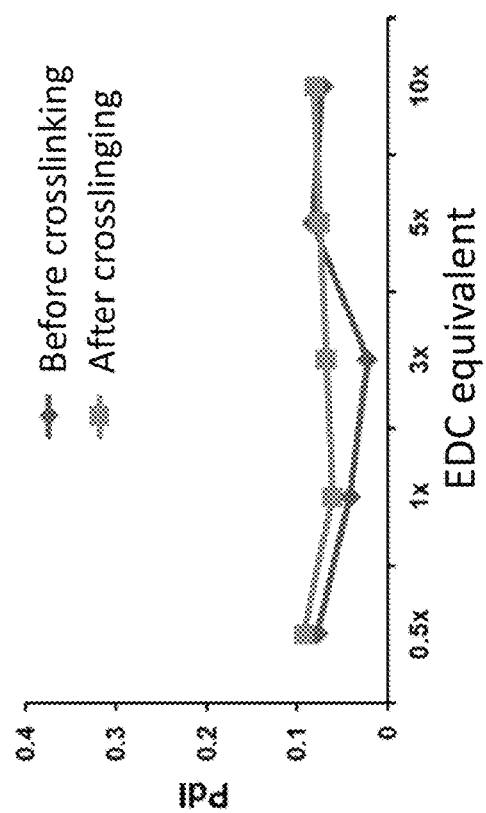
FIG. 9A shows the particle sizes of a polyion complex polymersome before and after crosslinking.
Figure 9B:
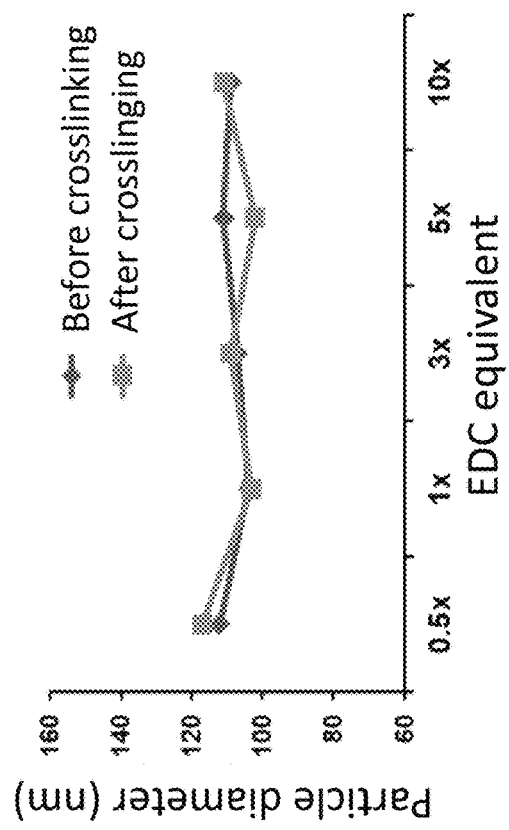
FIG. 9B shows polydispersity index (PDI) thereof.
Figure 9C:
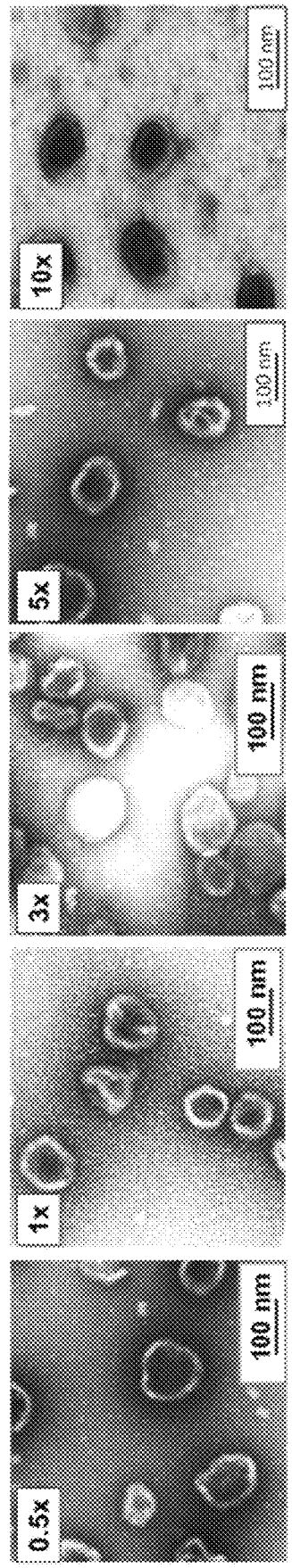
FIG. 9C shows TEM images thereof.

The relationship between the amount of EDC used in crosslinking and the particle size; the relationship between the amount of EDC and polydispersity (PDI); and the relationship between the amount of EDC and the shape of PICsome, are shown in FIGS. 9A-9C. These particle sizes, polydispersity values and shape (TEM image) were obtained in the same manner as in Examples 1 and 2 except that the amount of EDC was changed.

As a result, as shown in FIG. 9A, a significant difference was not observed in any amount of EDC in particle size (FIG. 9A), polydispersity (FIG. 9B) and PICsome shape (FIG. 9C). Also at any amount of EDC, the mono-dispersed particle size distribution was obtained with a particle size of 100 nm as a mode value.

Example 4: Molecular Weight of Substance to be Encapsulated and Shape of PICsome Obtained PEGs different in size up to a number average molecular weight of 6000 to 42000 were encapsulated in PICsomes. The shapes of the PICsomes obtained were observed.

PEG was labeled with fluorescein and encapsulated in PICsomes at a concentration of 0.5 mg/mL, 1 mg/mL, 3 mg/mL, 5 mg/mL, or 10 mg/mL in accordance with the method described in Example 1. The PEG used herein were PEG6 (MEPA-50H, manufactured by NOF Corporation Ltd.) having a number average molecular weight of 6 k; PEG12 (MEPA-12T, manufactured by NOF Corporation Ltd.) having a number average molecular weight of 12 k; PEG20 (MEPA-20T, manufactured by NOF Corporation Ltd.) having a number average molecular weight of 20 k; and PEG42 (MEPA-40T, manufactured by NOF Corporation Ltd.) having a number average molecular weight of 42 k.

As a result, as shown in FIG. 10, in the case where the concentration of PEG added was 5 mg/mL or less, PICsomes having a particle size of about 100 nm and a monodispersed particle size distribution were formed.

Example 5: Substance Permeability of Crosslinked PICsome

In this Example, PEG12 encapsulated PICsomes were prepared in the same manner as in Example 1 except that fluorescein-labelled PEG12 was used in a concentration of 4 mg/mL, and crosslinking was performed by varying the amount of EDC. Then, the amounts of PEG12 released from the PICsomes were examined.

The cumulative release amount of PEG12 from PEG12 encapsulated PICsomes, which were prepared by varying the EDC equivalent from Example 3 to control a crosslinking degree, was obtained by size exclusion chromatography and fluorescence intensity analysis. The size exclusion chromatography was performed by using a gel filtration chromatography column: Superdex 200-10/300GL, GE Healthcare, and high performance liquid chromatograph: LC-2000plus, manufactured by JASCO Corporation Ltd. The fluorescence intensity of fluorescein was compared between an early fraction having a shorter retention time (PEG encapsulated in PICsome) and a slow fraction having a longer retention time (released PEG) by a conventional method to obtain a cumulative release amount. As the solution, a 10 mM phosphate buffer solution (pH 7.4, 37° C.) was used. The results were as shown in FIG. 11A.

Figure 11A:
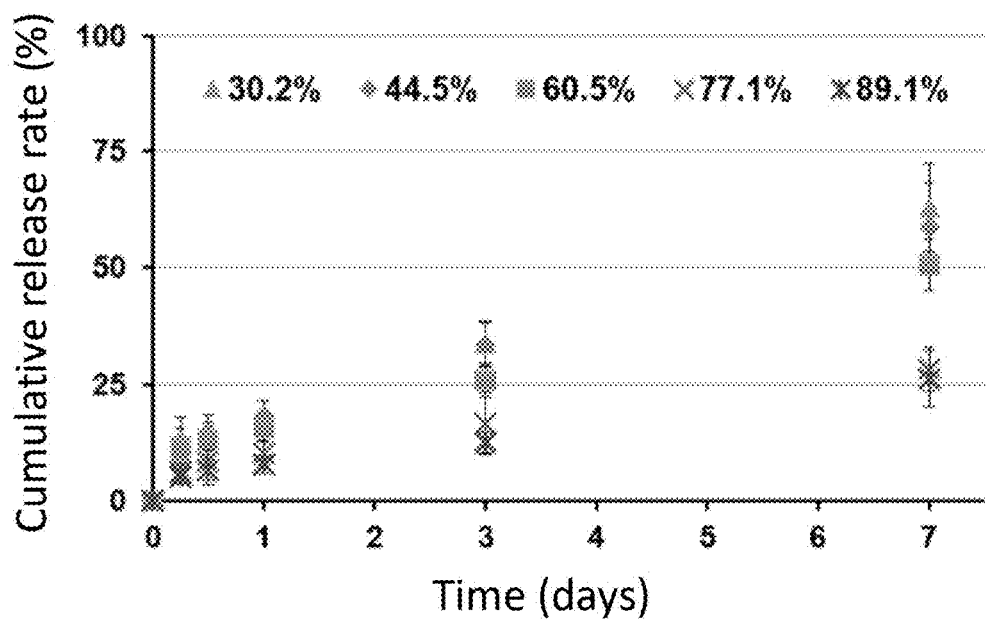
FIG. 11A shows a change of the release rates of a substance encapsulated from polyion complex polymersomes having various crosslinking degrees (%) (shown in the figure) with time.
Figure 11B:
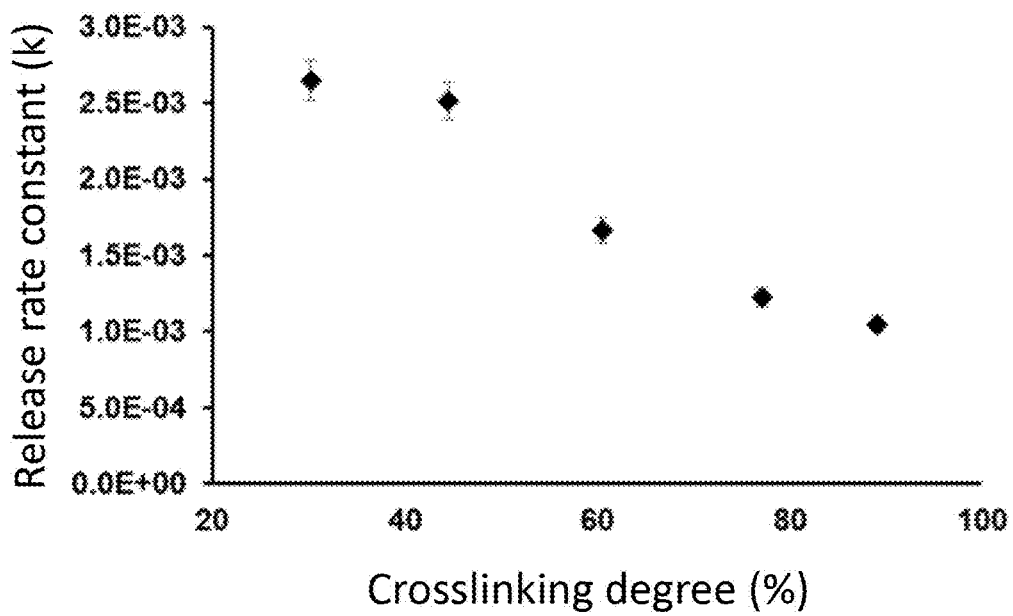
FIG. 11B shows the relationship between the crosslinking degree and the release rate constant.

As shown in FIG. 11A, the amount of PEG12 released from PICsomes varied depending upon the crosslinking degree. More specifically, the higher the crosslinking degree, the more PEG12 was held in PICsomes. When calculation was performed based on the release rate constant, the results were as shown in FIG. 11B. Note that, the release rate constant k was calculated by applying the results of cumulative release rate obtained to the following expression obtained from a primary release model.

$$\text{Log } C = \text{Log } C_0 - kt/2.303 \qquad \text{[Expression 2]}$$

where C represents the concentration of a substance encapsulated in a vesicle at time t: and $C_0$ represents the concentration of the substance encapsulated in the vesicle when t=0.

As shown in FIG. 11B, it was found that the higher the crosslinking degree, the smaller the release rate constant. It is observed that the release rate constant significantly changes before and after 45 to 60% of a crosslinking degree (FIG. 11B).

Next, dependency of a release rate constant on molecular weight was examined. In PICsomes having a low crosslinking degree (LC) of 40% or less and PICsomes having a high crosslinking degree (HC) of 80% or more, the release rates of PEG6, PEG20 and PEG42 were examined. PEGs were all labeled with fluorescein and the release rate constants were determined as described above. The results were as shown in FIG. 12.

Figure 12:
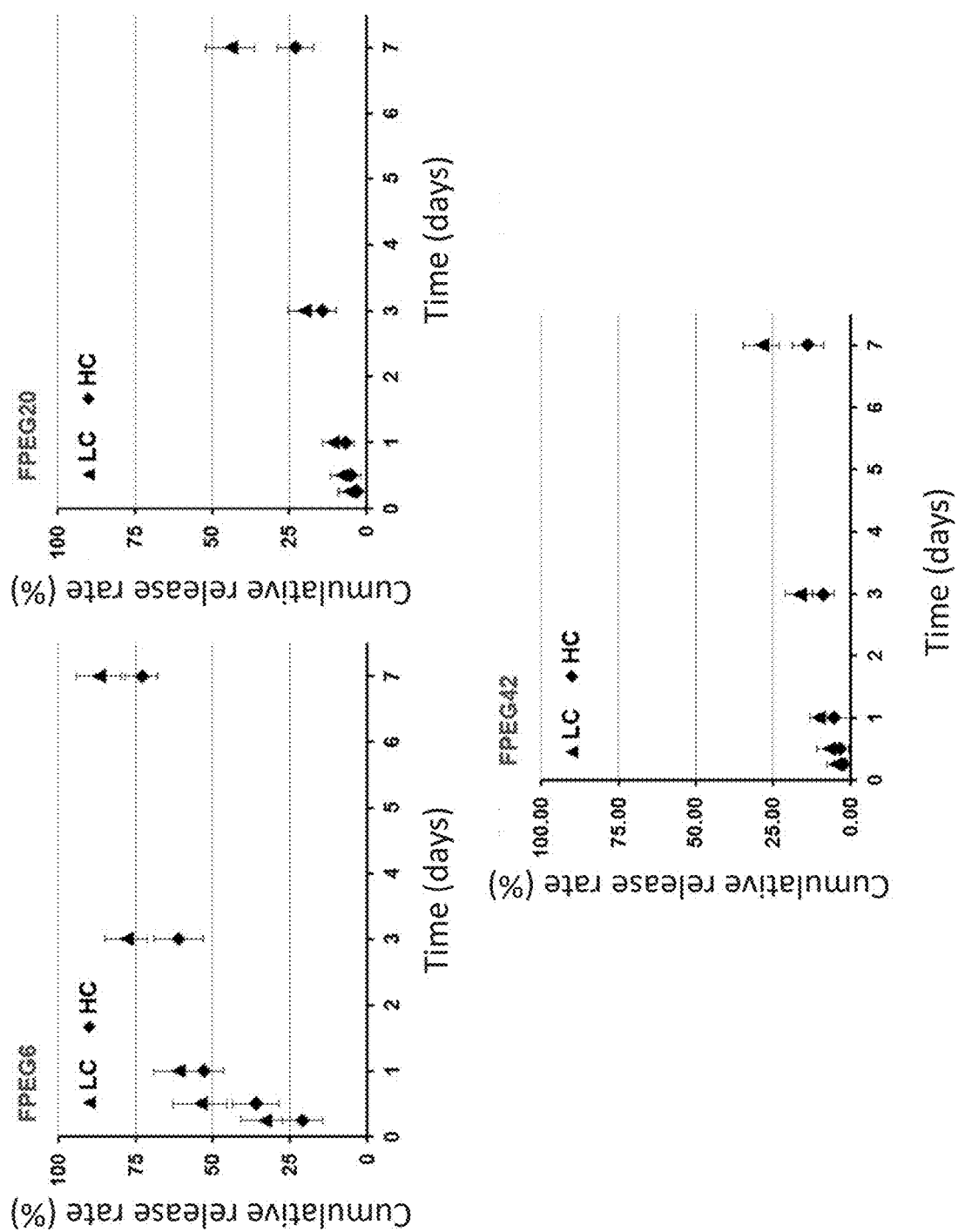
FIG. 12 shows a change of the release rates of polyethylene glycols (PEG) having various molecular weights from a polyion complex polymersome.

As shown in FIG. 12, in PEG6, a large amount of PEG was released from the PICsomes within a day; however, in PEG20 and PEG42, PEG was slowly released from the PICsomes at a constant rate from Day 0 to Day 7. The higher the crosslinking degree was, the more the release of PEG from PICsomes was suppressed. From this, it was found that small molecules easily pass through a PICsome and large molecules hardly pass through a PICsome. It was also found that the permeability of a molecule having a molecular weight of 6000 or less is relatively high; whereas the permeability of a molecule having a molecular weight of 20000 or more is relatively low.

Example 6: Relationship Between the Molecular Structure and Permeability of PICsome In the example, whether permeability of linear PEG and branched PEG through a PICsome differs or not was examined.

PICsomes were obtained in the same manner as in Example 1 except that PEG12 labeled with fluorescein was used in an amount of 4 mg/mL (concentration when it is mixed in a PICsome solution) as the linear PEG; whereas, PEG (PTE-100PA, manufactured by NOF Corporation Ltd., number average molecular weight 10 k) having four branches was used in an amount of 4 mg/mL (concentration when it is mixed in a PICsome solution) as branched PEG.

The cumulative release rate of PEG from a PICsome was determined in the same manner as in Example 5. The results were as shown in FIG. 13.

Figure 13:
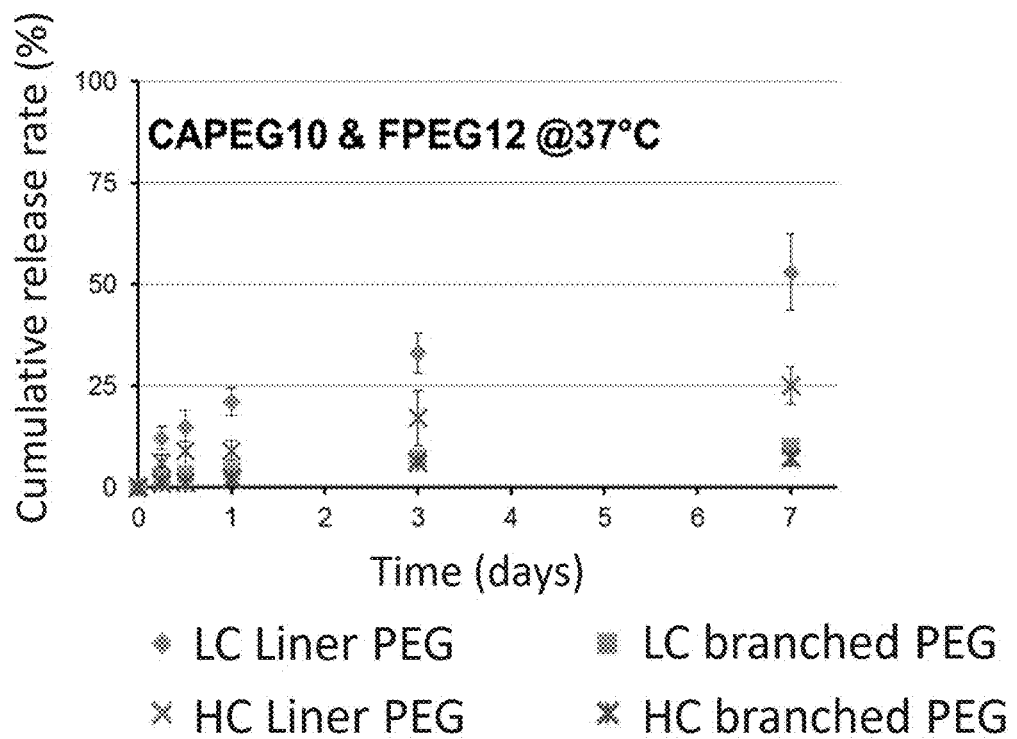
FIG. 13 shows difference in release rate between linear PEG and branched PEG.

As shown in FIG. 13, it was found that a branched PEG has a lower permeability through the membrane of a PICsome than a linear PEG.

Example 7: Temperature Dependency of Release Rate Constant

In Examples 5 and 6, release of a substance from a PICsome was examined at 37° C. In the example, temperature dependency of the release rate constant was revealed.

Fluorescein-labelled PEG6, PEG20 and PEG42 were encapsulated in PICsomes in the same manner as in Example 5 and the release rate constants were calculated under various temperature conditions. The results were as shown in FIGS. 14 and 15.

Figure 14:
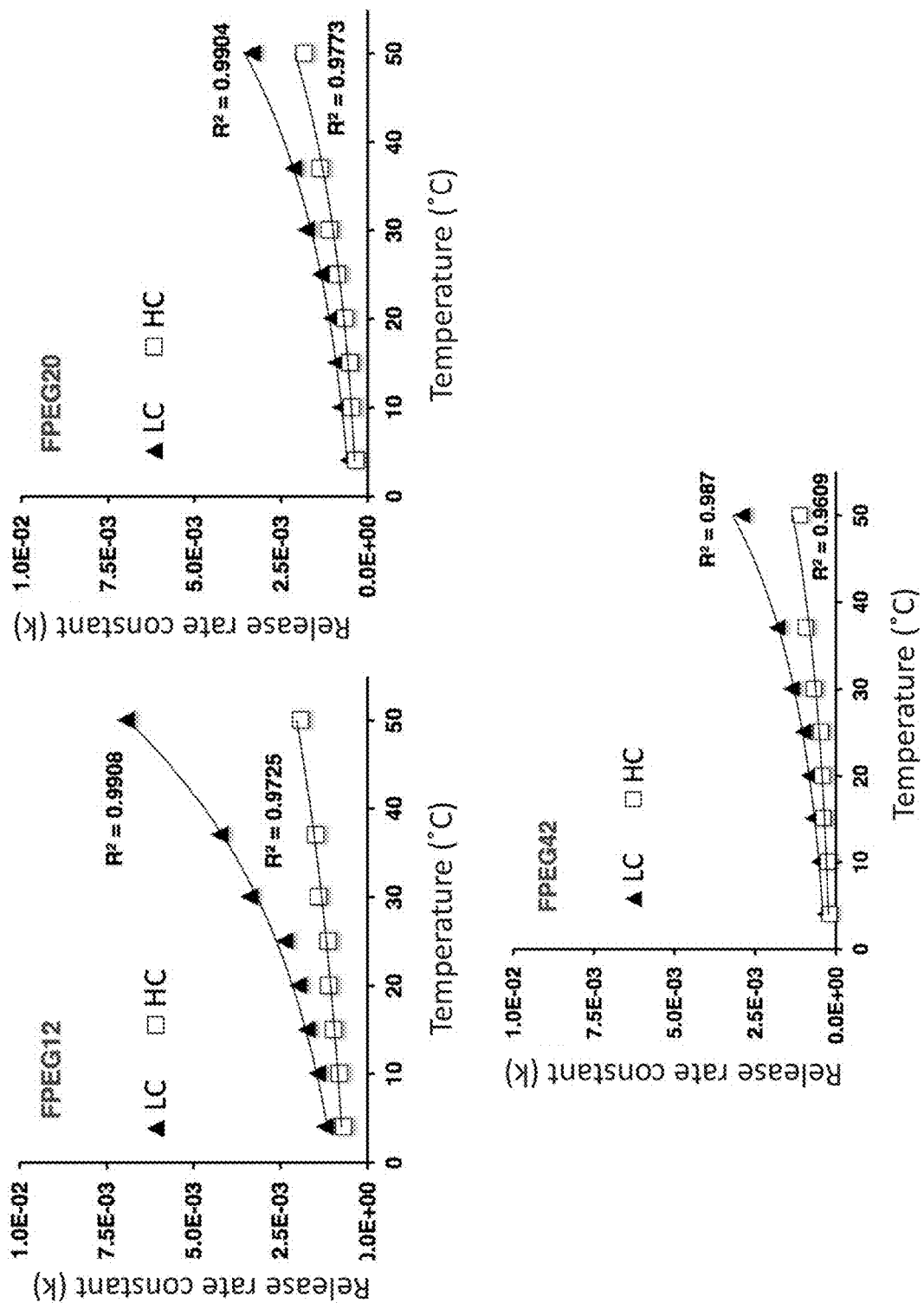
FIG. 14 shows the relationship between the release rate constant of PEG from a polyion complex polymersome and temperature. In the figure, "LC" indicates the release rate from a polyion complex polymersome having a crosslinking degree of less than 40%; and "HC" indicates the release rate from a polyion complex polymersome having a crosslinking degree of 80% or more.
Figure 15:
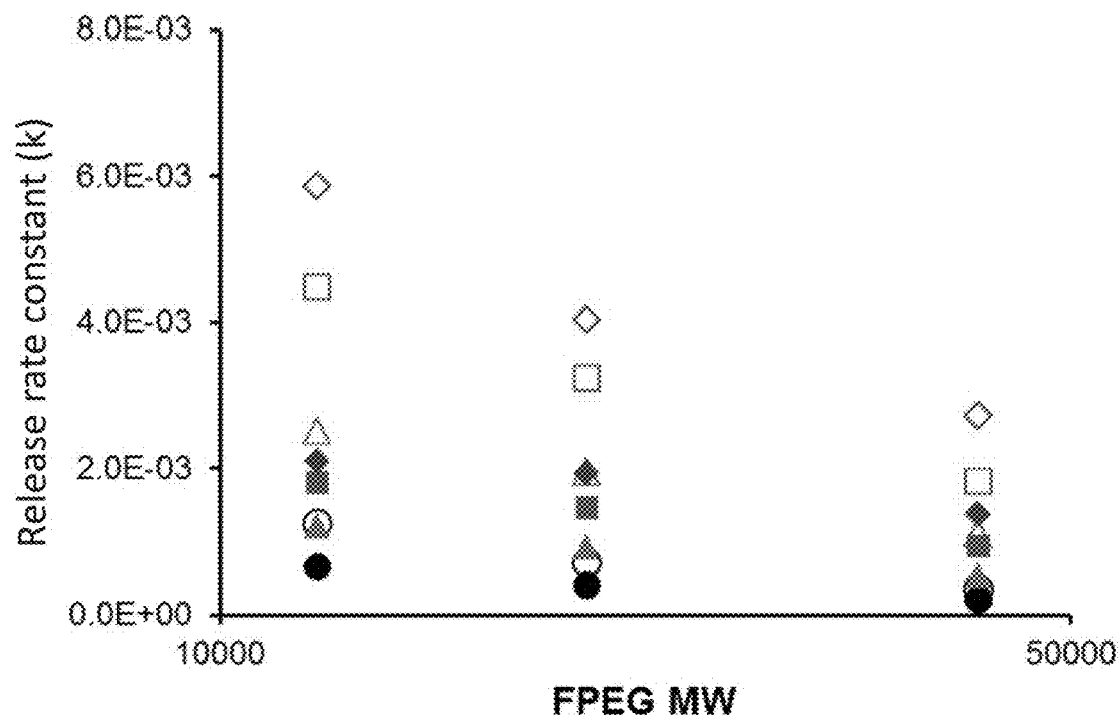
FIG. 15 shows the relationship between the molecular weight of PEG and release rate constant thereof.

As shown in FIGS. 14 and 15, temperature dependency of the release rate constant was remarkable in the PICsome having a low crosslinking degree of less than 40%. Note that, in FIG. 15, a circle represents the release rate constant at 4° C., a triangle at 25° C., a square at 37° C. and a rhombus at 50° C.; and open marks indicate the release rate constants of PICsomes having low crosslinking degrees; whereas solid marks indicate the release rate constants of PICsomes having high crosslinking degrees.

$$\frac{M_t}{M_\infty} = 1 - \frac{8}{\pi^2}\exp(-D\pi^2 t/4l^2) \quad \text{[Expression 3]}$$

where the left-hand side represents the cumulative release amount (%) at time t; D represents the diffusion coefficient of a substance encapsulated, in PICsome membrane; and l represents the thickness (up to 15 nm) of the PICsome membrane.

Figure 16:
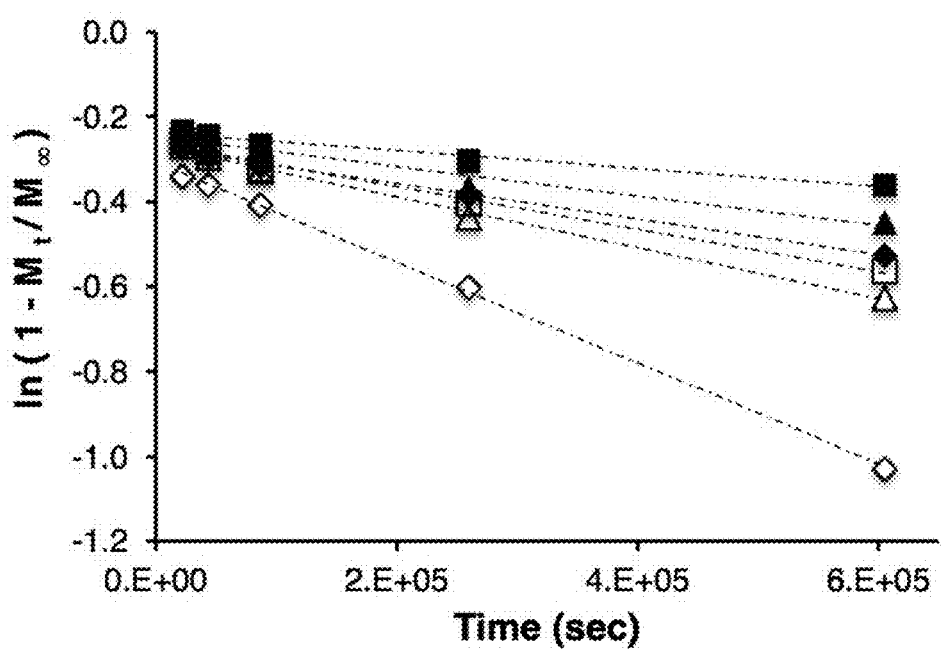
FIG. 16 shows the cumulative release amount at time t (%) and time t. In the figure, the slopes of the lines are in proportional to the diffusion coefficient of a molecule in the membrane in a polyion complex polymersome.

According to the above expression, the cumulative release amount (at time t) and time t are plotted on a logarithmic chart to obtain the graph of FIG. 16 showing the relationship between them. In the graph herein, the slopes of the lines are in proportional to D. The symbols in FIG. 16 are the same as defined in FIG. 15.

As shown in FIG. 16, it was found that the diffusion coefficient is higher in PICsome membrane having a low crosslinking degree.

From these Examples, it was suggested that a nonlinear protein having a molecular weight exceeding 10,000 can be effectively maintained within a PICsome; whereas, a molecule having a small molecular weight of several thousands (or less), preferably 1000 or less, can efficiently pass through the PICsome.

It was also found that if an enzyme having a large molecular weight which acts on a substrate having a small molecular weight is encapsulated in PICsomes to dramatically improve in blood retention by taking advantage of such properties of PICsomes, the PICsomes stably maintain the enzyme encapsulated therein, in the blood and allow the enzyme to continuously react with a substrate present in the blood.

L-ASP is known to have a growth inhibitory effect on asparagine-requiring tumor cells and used as a pediatric acute lymphoblastic leukemia therapeutic agent in clinical sites. From this Example, it is demonstrated that the L-ASP encapsulated PICsome of the present invention exerts a high effect as a pediatric acute lymphoblastic leukemia therapeutic agent.

Example 8A: Encapsulation of Other Enzymes and Stability Evaluation

In this Example, the blood stability of α-galactosidase, α-glucosidase and uricase was examined.

1. Preparation of Solution of α-GAL Encapsulated PICsome

In the same manner as in Section 5 of Example 1, a solution containing empty PICsomes was prepared. Thereafter, 11.4 mg of α-galactosidase (hereinafter referred to as "α-GAL") was dissolved in 5.7 mL of a 10 mM phosphate buffer (PB, pH 7.4, 0 mM NaCl) to prepare a 2 mg/mL α-GAL solution.

An aliquot (1 mL) was taken from the 2 mg/mL α-GAL solution and mixed with 1 mL of the solution containing empty PICsomes. The solution mixture was stirred by a Vortex mixer for 2 minutes (2000 rpm). Thereafter, to the solution, a PB solution (5.6 mL) containing a water soluble condensing agent, EDC (10 mg/mL) was added. The mixture was allowed to stand still overnight to crosslink a polyion complex. Thereafter, a polymer not involved in formation of PICsomes, α-GAL not encapsulated in the PICsomes, EDC and others were removed by use of an ultrafiltration tube with membrane having fractionation molecular weight of 300,000. A solution of fluorescence labeled α-GAL was prepared in the same manner as above.

α-Glucosidase encapsulated PICsomes and uricase encapsulated PICsomes were prepared in the same manner as above.

A solution containing empty PICsomes was prepared in the same manner as above. Thereafter, α-glucosidase (6.2 mg) and uricase (10.4 mg) were dissolved in 3.1 mL and 5.2 mL of 10 mM phosphate buffer (PB, pH 7.4, 0 mM NaCl), respectively, to prepare a 2 mg/mL α-glucosidase solution and a 2 mg/mL uricase solution.

The 2 mg/mL α-glucosidase solution and 2 mg/mL uricase solution were separately mixed with 1 mL of the solution containing empty PICsomes. The resultant solutions were separately stirred by a Vortex mixer for 2 minutes (2000 rpm). Thereafter, a PB solution (5.6 mL) containing a water soluble condensing agent, EDC (10 mg/mL), was added. The resultant mixtures were allowed to stand still overnight to crosslink a polyion complex. Thereafter, a polymer not involved in formation of PICsomes, α-glucosidase and uricase not encapsulated in PICsomes, EDC and others, were removed by use of an ultrafiltration tube with membrane having fractionation molecular weight of 300,000. Solutions of fluorescence labeled α-glucosidase and uricase were prepared in the same manner as above.

2. Evaluation of α-GAL Encapsulated PICsome by Zetasizer

Figure 17A:
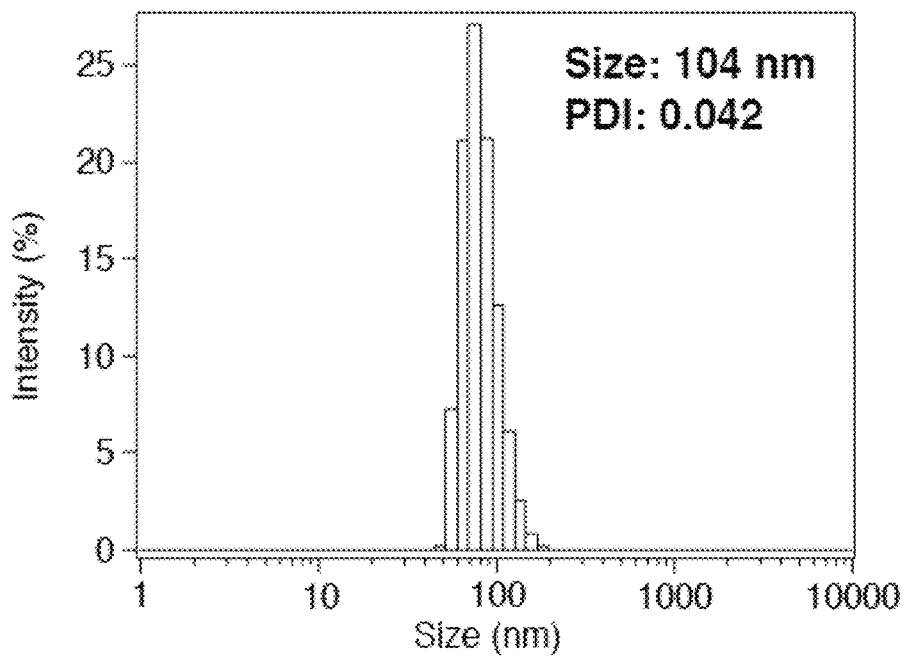
FIG. 17A shows the particle size distribution of PICsomes encapsulating α-galactosidase (hereinafter also referred to as "α-GAL")

As described in Section 1 of Example 2, the size (Z average particle diameter) and polydispersity index (PDI) of the α-GAL encapsulated PICsomes obtained were measured by Zetasizer (Malvern). The size was obtained by measuring diffusion of particles moving in accordance with the Brownian motion and converting the measurement results to a particle size and a particle size distribution in accordance with the Stokes-Einstein equation. The results were as shown in FIG. 17A. As shown in FIG. 17A, mono-dispersed PICsomes uniform in size were obtained similarly to L-ASP encapsulated PICsomes.

3. Confirmation that α-GAL is Encapsulated in PICsome

Figure 17B:
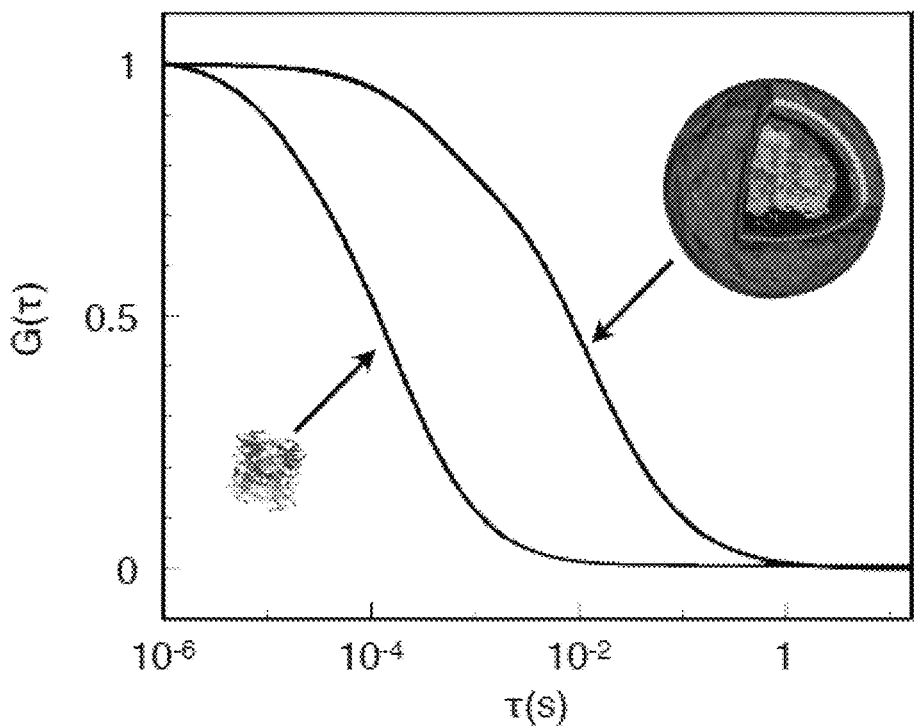
FIG. 17B shows the analytical results of unencapsulated free (α-galactosidase and α-galactosidase encapsulated in PICsome, by fluorescence correlation spectroscopy.

As described in Section 2 of Example 2, to confirm that α-GAL is encapsulated in a PICsome, the molecular diffusion rates of solutions of free α-GAL and encapsulated α-GAL were evaluated by fluorescence correlation spectroscopy (FCS). The results were as shown in FIG. 17B. As shown in FIG. 17B, the diffusion time and fluorescence intensity per particle of encapsulated α-GAL are higher than those of the free α-GAL. From this, it was confirmed that α-GAL is encapsulated in a PICsome without fail. Also, as shown in Table 1, from comparison of fluorescence intensity per particle, it was estimated that three molecules of α-GAL are encapsulated in a single PICsome.

Figure 18:
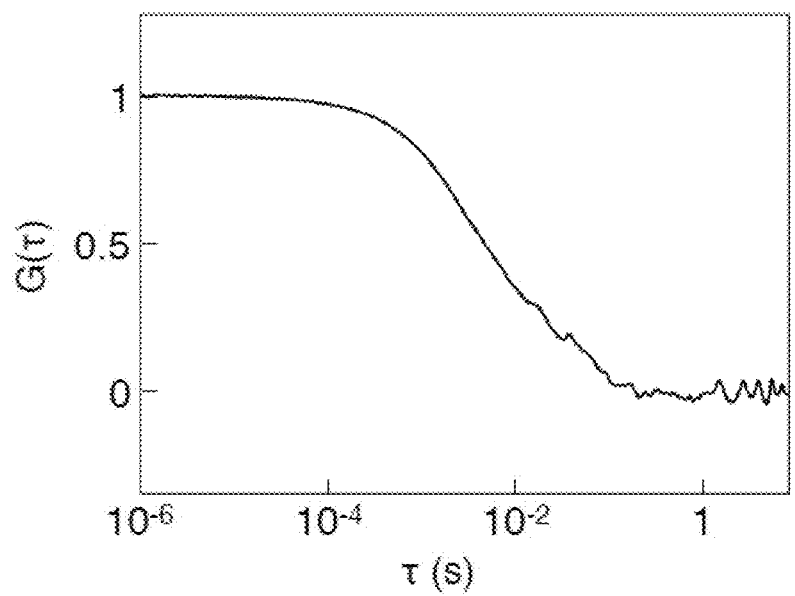
FIG. 18 shows analytical results of α-glucosidase and uricase encapsulated in PICsomes by fluorescence correlation spectroscopy.
Figure 18:
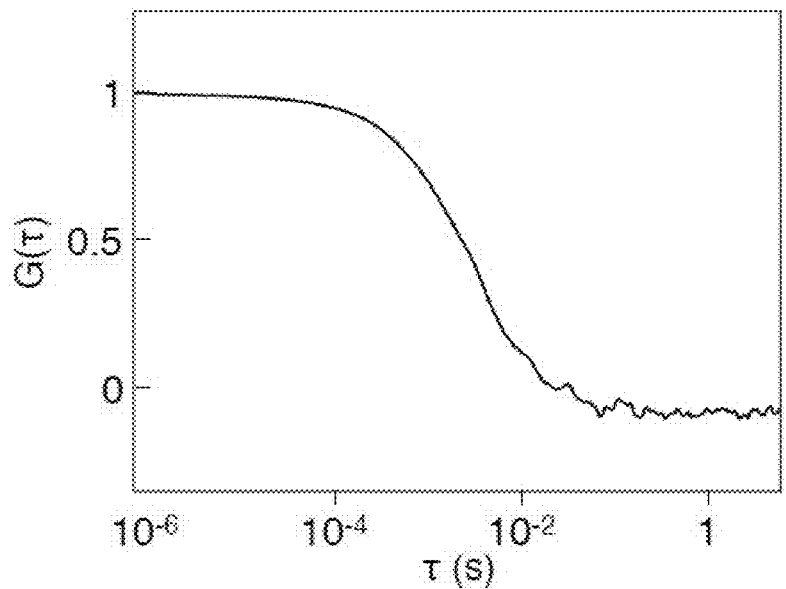

Further, it was confirmed that α-glucosidase and uricase were each encapsulated in PICsomes, by fluorescence correlation spectroscopy (FCS) (FIG. 18).

TABLE 1

| | Count per molecule |
|---|---|
| D488-α-GAL | 44.5 ± 5.1 |
| PICsome encapsulating D488-α-GAL | 138.8 ± 4.2 |

4. Blood Retention of α-GAL Encapsulated in PICsome

Figure 19A:
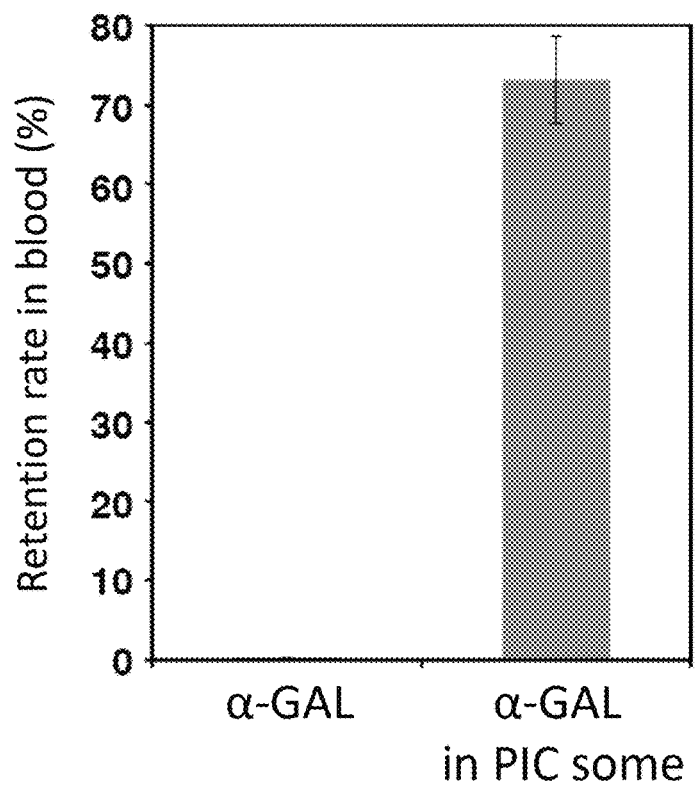
FIG. 19A shows blood retention of α-GAL encapsulated in PICsomes.

As described in Section 3 of Example 2, blood retention of free α-GAL and encapsulated α-GAL was evaluated. To mice (Balb/c, 6 weeks old, n=3), a PICsome encapsulating a Cy5-α-GAL was administered through the tail vein. Twelve hours later, blood was sampled and the fluorescence intensity of the supernatant (Ex/Em=650 nm/670 nm) was measured. The results were as shown in FIG. 19A. As shown in FIG. 19A, the blood retention of encapsulated α-GAL was remarkably high, compared to that of free α-GAL.

5. Maintenance of Enzyme Activity Under Physiological Conditions

Figure 19B:
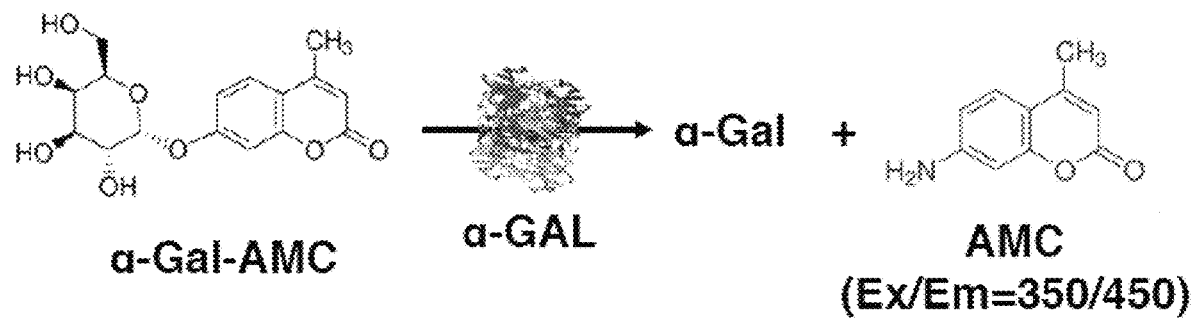
FIG. 19B shows a measurement scheme of enzyme activity.

Enzyme activity was evaluated with respect to free α-GAL and encapsulated α-GAL, respectively. The enzyme activity of α-GAL was checked by the reaction with a substrate, α-galactosyl-β-(7-amide-4-methyl coumarin) (also referred to as "Gal-AMC") as shown in FIG. 19B. Gal-AMC is decomposed by the enzyme activity of α-GAL to produce 7-amino-4-methyl coumarin (also referred to as "AMC"), which emits fluorescence (Ex/Em=350 nm/450 nm).

More specifically, first, PBS solutions of Gal-AMC, free α-GAL, and encapsulated α-GAL were each placed in a thermostatic chamber and allowed to stand still at 37° C. Thereafter, the Gal-AMC solution was mixed with the free α-GAL or encapsulated α-GAL solution. From the solution mixture, an aliquot (predetermined amount) was taken and immediately poured to a 96 well plate (TECAN). The plate was placed in a multiplate reader kept at 37° C. in advance and fluorescence intensity was measured periodically for a predetermined time.

The enzyme activity was evaluated by preparing the Michaelis-Menten plot and Lineweaver-Burk plot. At this time, using a calibration curve previously prepared by using an AMS standard solution, a change of fluorescence intensity was converted into the production rate of a product. In this manner, a reaction rate V was obtained. Measurement was performed by changing the substrate concentration [S] variously. [S] was plotted on the horizontal axis and V was plotted on the vertical axis. The plot results were applied to the expression to calculate the Michaelis-Menten coefficient ($K_m$). The results were as shown in Table 2.

TABLE 2

| | Km (mM) |
|---|---|
| α-GAL | 0.18 |
| α-GAL encapsulated in PICsome | 0.19 |

As shown in Table 2, α-GAL encapsulated in a PICsome was stable in vivo and maintains the same enzyme activity as in free α-GAL.

The invention claimed is:

1. A method for treating an asparagine-requiring tumor, comprising:
   administering an effective amount of a pharmaceutical composition comprising a polyion complex polymersome encapsulating L-asparaginase to a patient in need thereof,
   wherein the polyion complex polymersome comprises a polymer of formula (I),

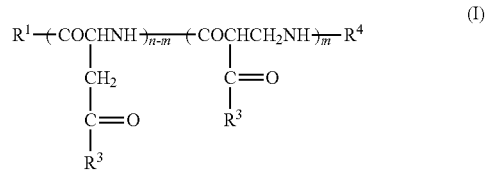

where $R^1$ is a hydroxyl group, a protecting group, a hydrophobic group or a polymerizable group, $R^4$ is H, a protecting group, a hydrophobic group or a polymerizable group, $R^3$ is a group represented by —(NH—$(CH_2)_2$)$_2$—$NH_2$ and n is an integer of 0 to 5000 and in is an integer of 0 to 5000, provided that m+n is an integer of 2 to 5000, and that n–m is an integer of 0 or more.

2. The method according to claim 1, wherein the asparagine-requiring tumor is a tumor in which an expression level of an asparagine-producing enzyme is 80% or less of an expression level of an asparagine-producing enzyme in a normal cell.

3. The method according to claim 1, wherein the asparagine-requiring tumor is selected from the group consisting of acute lymphocytic leukemia, T cell malignant lymphoma, NK cellular leukemia and acute myelogenous leukemia.

4. The method according to claim 1, wherein the administering of the pharmaceutical composition induces hydrolysis of L-asparagine in the blood of the patient.

5. A method for administering L-asparaginase, comprising:
   administering to a subject a pharmaceutical composition comprising a polyion complex polymersome encapsulating L-asparaginase such that the L-asparaginase is administered to the subject, wherein the polyion complex polymersome comprises a polymer of formula (I):

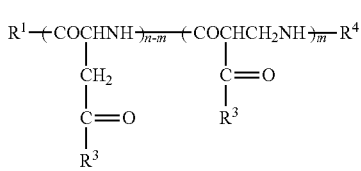

where $R^1$ is a hydroxyl group, a protecting group, a hydrophobic group or a polymerizable group, $R^4$ is H, a protecting group, a hydrophobic group or a polymerizable group, $R^3$ is a group represented by —(NH—(CH$_2$)$_2$)$_2$—NH$_2$, and n is an integer of 0 to 5000 and m is an integer of 0 to 5000, provided that m+n is an integer of 2 to 5000, and that n−m is an integer of 0 or more.

6. The method according to claim 5, wherein the administering of the pharmaceutical composition induces hydrolysis of L-asparagine in the blood in the subject.

7. A method for treating an asparagine-requiring tumor, comprising:
administering an effective amount of a pharmaceutical composition comprising a polyion complex polymersome encapsulating L-asparaginase to a patient in need thereof,
wherein the polyion complex polymersome includes a plurality of anionic polymers, a plurality of cationic polymers, and a plurality of crosslinks crosslinking the anionic polymers and the cationic polymers forming a membrane of the polyion complex polymersome, and the cationic polymers are a polymer of formula (I)

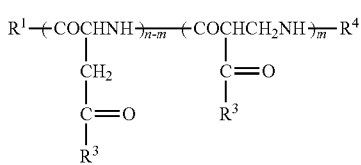

where $R^1$ is a hydroxyl group, a protecting group, a hydrophobic group or a polymerizable group, $R^4$ is H, a protecting group, a hydrophobic group or a polymerizable group, $R^3$ is a group represented by —(NH—(CH$_2$)$_2$)$_2$—NH$_2$, and n is an integer of 0 to 5000 and m is an integer of 0 to 5000, provided that m+n is an integer of 2 to 5000, and that n−m is an integer of 0 or more.

8. The method of claim 7, wherein in measurement in a 10 mM phosphate buffer solution of pH 7.4 at 37° C., a release rate constant k of a linear polyethylene glycol having a number average molecular weight of 2 kDa from the polyion complex polymersome is $5 \times 10^{-3}$ or less.

9. The method of claim 7, wherein the membrane of the polyion complex polymersome has a permeability which allows asparagine to pass through the membrane of the polyion complex polymersome.

10. The method of claim 9, wherein the L-asparaginase is enzymatically active in the polyion complex polymersome.

11. The method of claim 10, wherein the L-asparaginase hydrolyzes asparagine passed through the membrane of the polyion complex polymersome and comes in contact with the L-asparaginase in the polyion complex polymersome.

12. The method of claim 9, wherein at least one of the plurality of anionic polymers and the plurality of cationic polymers forms a block co-polymer with a polyethylene glycol segment.

13. The method of claim 5, wherein the polyion complex polymersome includes anionic polymers, cationic polymers and a plurality of crosslinks crosslinking the anionic and cationic polymers, and the cationic polymers are the polymer of formula (I).

14. The method of claim 13, wherein in measurement in a 10 mM phosphate buffer solution of pH 7.4 at 37° C., a release rate constant k of a linear polyethylene glycol having a number average molecular weight of 2 kDa from the polyion complex polymersome is $5 \times 10^{-3}$ or less.

15. The method of claim 13, wherein the membrane of the polyion complex polymersome has a permeability which allows asparagine to pass through the membrane of the polyion complex polymersome.

16. The method of claim 15, wherein the L-asparaginase is enzymatically-active in the polyion complex polymersome.

17. The method of claim 16, wherein the L-asparaginase hydrolyzes asparagine passed through the membrane of the polyion complex polymersome and comes in contact with the L-asparaginase in the polyion complex polymersome.

18. The method of claim 13, wherein the polyion complex polymersome comprises a polycation and a polyanion, and at least one of the polycation and polyanion forms a block co-polymer with a polyethylene glycol segment, and the polycation is the polymer of formula (I).

19. The method of claim 9, wherein in measurement in a 10 mM phosphate buffer solution of pH 7.4 at 37° C., a release rate constant k of a linear polyethylene glycol having a number average molecular weight of 2 kDa from the polyion complex polymersome is $5 \times 10^{-3}$ or less.

20. The method of claim 6, wherein the membrane of the polyion complex polymersome has a permeability which allows asparagine to pass through the membrane of the polyion complex polymersome.

21. The method of claim 5, wherein the L-asparaginase is enzymatically active in the polyion complex polymersome.

22. The method of claim 5, wherein the L-asparaginase hydrolyzes asparagine passed through the membrane of the polyion complex polymersome and comes in contact with the L-asparaginase in the polyion complex polymersome.

23. The method of claim 19, wherein at least one of the plurality of anionic polymers and the plurality of cationic polymers forms a block co-polymer with a polyethylene glycol segment.

24. The method of claim 1, wherein in measurement in a 10 mM phosphate buffer solution of pH 7.4 at 37° C., a release rate constant k of a linear polyethylene glycol having a number average molecular weight of 2 kDa from the polyion complex polymersome is $5 \times 10^{-3}$ or less.

25. The method of claim 1, wherein the membrane of the polyion complex polymersome has a permeability which allows asparagine to pass through the membrane of the polyion complex polymersome.

26. The method of claim 1, wherein the L-asparaginase is enzymatically active in the polyion complex polymersome.

27. The method of claim 1, wherein the L-asparaginase hydrolyzes asparagine passed through a membrane of the polyion complex polymersome and comes in contact with the L-asparaginase in the polyion complex polymersome.

28. The method of claim 3, wherein in measurement in a 10 mM phosphate buffer solution of pH 7.4 at 37° C., a release rate constant k of a linear polyethylene glycol having a number average molecular weight of 2 kDa from the polyion complex polymersome is $5 \times 10^{-3}$ or less.

29. The method of claim 3, wherein the membrane of the polyion complex polymersome has a permeability which allows asparagine to pass through the membrane of the polyion complex polymersome.

30. The method of claim 3, wherein the L-asparaginase is enzymatically active in the polyion complex polymersome.

31. The method of claim 3, wherein the L-asparaginase hydrolyzes asparagine passed through a membrane of the polyion complex polymersome and comes in contact with the L-asparaginase in the polyion complex polymersome.

32. The method of claim 8, wherein the plurality of cationic polymers forms a block co-polymer with a polyethylene glycol segment.

33. The method according to claim 7, wherein the asparagine-requiring tumor is a tumor in which an expression level of an asparagine-producing enzyme is 80% or less of an expression level of an asparagine-producing enzyme in a normal cell.

34. The method according to claim 7, wherein the asparagine-requiring tumor is selected from the group consisting of acute lymphocytic leukemia, T cell malignant lymphoma, NK cellular leukemia and acute myelogenous leukemia.

35. The method according to claim 12, wherein the asparagine-requiring tumor is a tumor in which an expression level of an asparagine-producing enzyme is 80% or less of an expression level of an asparagine-producing enzyme in a normal cell.

36. The method according to claim 12, wherein the asparagine-requiring tumor is selected from the group consisting of acute lymphocytic leukemia, T cell malignant lymphoma, NK cellular leukemia and acute myelogenous leukemia.

37. The method of claim 7, wherein the plurality of cationic polymers forms a block co-polymer with a polyethylene glycol segment.

* * * * *